United States Patent
Mizutani et al.

(10) Patent No.: US 12,427,156 B2
(45) Date of Patent: Sep. 30, 2025

(54) SOLID DOSAGE FORM HAVING EXCELLENT STABILITY

(71) Applicant: Shionogi & Co., Ltd., Osaka (JP)

(72) Inventors: Naoya Mizutani, Hyogo (JP); Masayuki Morimoto, Hyogo (JP); Maki Okabe, Osaka (JP); Masaaki Ito, Hyogo (JP); Go Kimura, Hyogo (JP)

(73) Assignee: SHIONOGI & CO., LTD., Osaka (JP)

( * ) Notice: Subject to any disclaimer, the term of this patent is extended or adjusted under 35 U.S.C. 154(b) by 0 days.

(21) Appl. No.: 18/435,082

(22) Filed: Feb. 7, 2024

(65) Prior Publication Data

US 2024/0252505 A1 Aug. 1, 2024

Related U.S. Application Data

(63) Continuation of application No. 17/077,606, filed on Oct. 22, 2020, now Pat. No. 11,925,648, which is a continuation of application No. PCT/JP2019/017146, filed on Apr. 23, 2019.

(30) Foreign Application Priority Data

Apr. 24, 2018 (JP) ................................ 2018-083006

(51) Int. Cl.

| A61K 31/5383 | (2006.01) |
|---|---|
| A61K 9/16 | (2006.01) |
| A61K 47/02 | (2006.01) |
| A61K 47/12 | (2006.01) |
| A61K 47/14 | (2017.01) |
| A61K 47/22 | (2006.01) |
| A61K 47/26 | (2006.01) |
| A61K 47/38 | (2006.01) |

(52) U.S. Cl.
CPC ........ *A61K 31/5383* (2013.01); *A61K 9/1611* (2013.01); *A61K 9/1623* (2013.01); *A61K 9/1635* (2013.01); *A61K 9/1652* (2013.01); *A61K 47/02* (2013.01); *A61K 47/12* (2013.01); *A61K 47/14* (2013.01); *A61K 47/22* (2013.01); *A61K 47/26* (2013.01); *A61K 47/38* (2013.01)

(58) Field of Classification Search
CPC ... A61K 31/5383; A61K 9/1611; A61K 47/02
See application file for complete search history.

(56) References Cited

U.S. PATENT DOCUMENTS

| 6,458,389 B1 | 10/2002 | Debregeas et al. |
|---|---|---|
| 2008/0014321 A1 | 1/2008 | Schweinfurth et al. |
| 2011/0293670 A1 | 12/2011 | Matsuzawa et al. |
| 2020/0375998 A1 | 12/2020 | Hayashi et al. |

FOREIGN PATENT DOCUMENTS

| CA | 3 008 607 | 6/2017 |
|---|---|---|
| CA | 3 033 180 | 2/2018 |
| CN | 102281879 | 12/2011 |
| CN | 108440564 | 8/2018 |
| EP | 2 213 304 | 8/2010 |
| EP | 3 290 424 | 3/2018 |
| EP | 3 428 170 | 1/2019 |
| EP | 3 473 629 | 4/2019 |
| EP | 3 498 281 | 6/2019 |
| EP | 3 693 373 | 8/2020 |
| JP | 9-249563 | 9/1997 |
| JP | 2000-34227 | 2/2000 |
| JP | 2001-512433 | 8/2001 |
| JP | 2007-269783 | 10/2007 |
| JP | 2008-7420 | 1/2008 |
| JP | 2009-536940 | 10/2009 |
| JP | 2013-523757 | 6/2013 |
| JP | 2014-534215 | 12/2014 |
| JP | 2016-79102 | 5/2016 |
| WO | 99/59572 | 11/1999 |
| WO | 2007/132907 | 11/2007 |
| WO | 2009/044854 | 4/2009 |
| WO | 2011/123496 | 10/2011 |
| WO | 2013/066616 | 5/2013 |
| WO | 2016/175224 | 11/2016 |
| WO | 2019-098259 | 5/2019 |

OTHER PUBLICATIONS

International Search Report issued Jul. 2, 2019 in International Patent Application No. PCT/JP2019/017146.
Young-A Heo, "Baloxavir: First Global Approved", Drugs, vol. 78, No. 6, pp. 693-697 (2018).
"Report on the Deliberation Result", Pharmaceutical Evaluation Division, Pharmaceutical Safety and Environmental Health Bureau, Ministry of Health, Labour and Welfare, Feb. 8, 2018, pp. 1-88.
Search Report dated Mar. 10, 2023 in corresponding Chinese Patent Application No. 201980038190.7, with English language translation.
First Office Action issued Mar. 17, 2023 in corresponding Chinese Patent Application No. 201980038190.7, with English language translation.
English Translation of International Preliminary Report on Patentability mailed Nov. 5, 2020 in corresponding International (PCT) Patent Application No. PCT/JP2019/017146.

*Primary Examiner* — Kamal A Saeed
(74) *Attorney, Agent, or Firm* — WENDEROTH, LIND & PONACK, L.L.P.

(57) ABSTRACT

The present invention provides a solid dosage form having good stability, suspensibility in water and fluidity by preparing a solid dosage form containing a compound represented by formula (I) or a pharmaceutically acceptable salt thereof, a stabilizer, a sugar alcohol and/or a sugar, a water-soluble polymer and an inorganic substance.

14 Claims, 2 Drawing Sheets

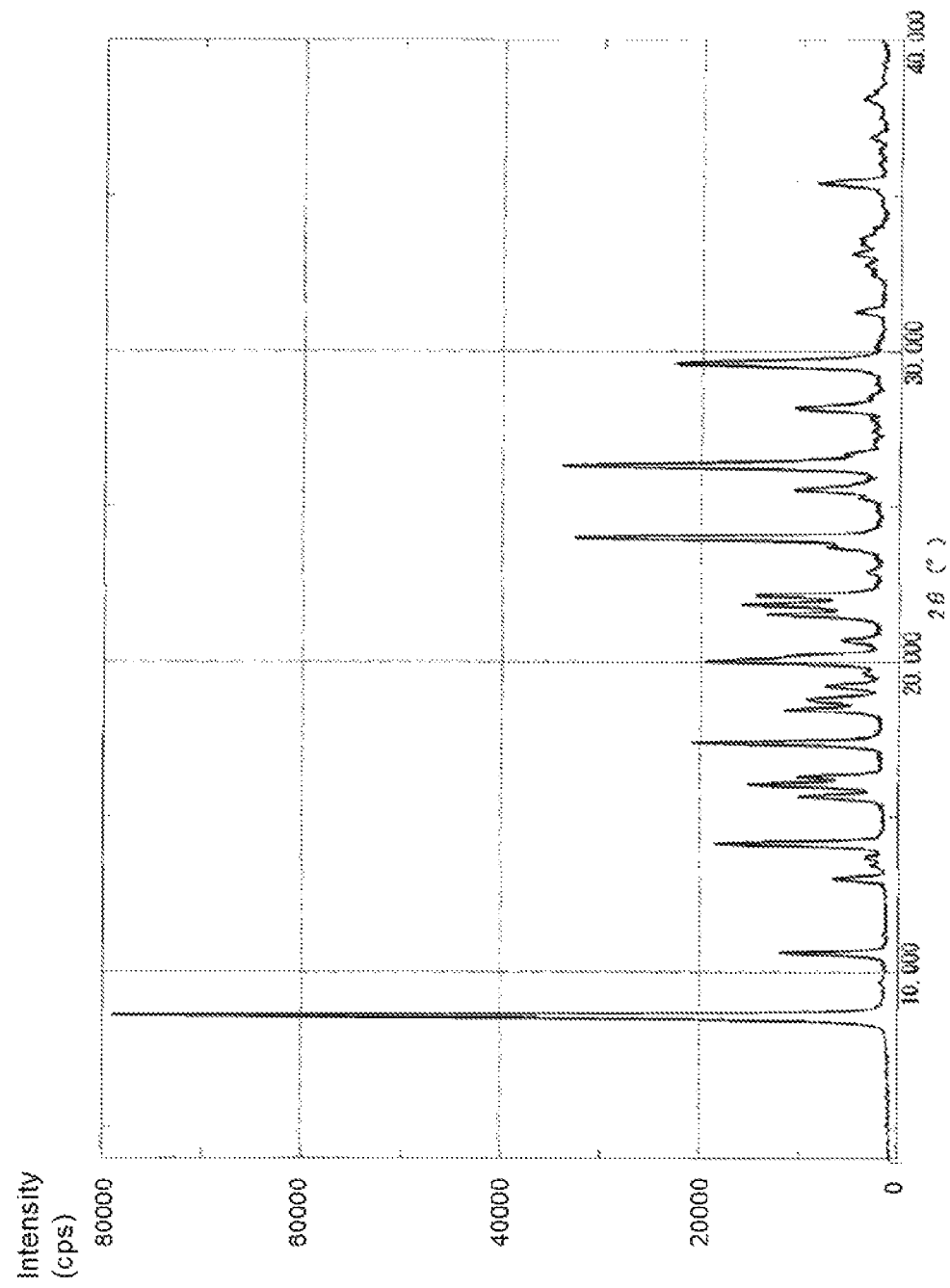
[Fig. 1]

[Fig. 2]
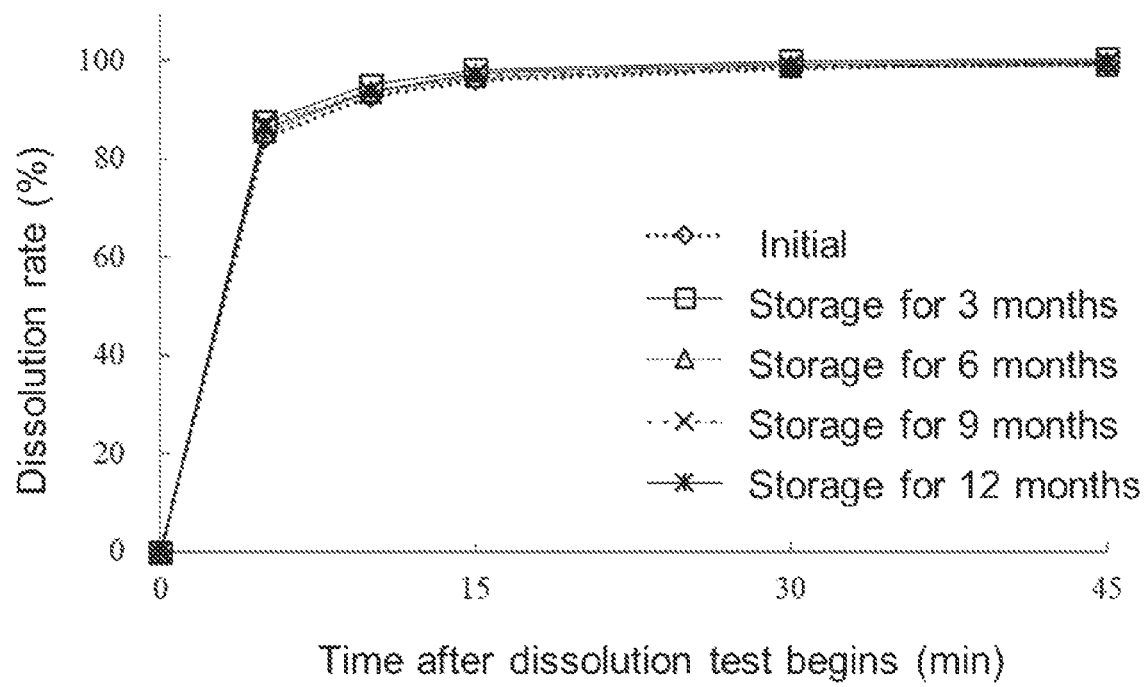

SOLID DOSAGE FORM HAVING EXCELLENT STABILITY

CROSS-REFERENCE TO RELATED APPLICATIONS

This application is a continuation application of U.S. application Ser. No. 17/077,606, filed Oct. 22, 2020, which is a continuation application of International Patent Application No. PCT/JP2019/017146, filed Apr. 23, 2019, which claims priority to Japan Patent Application No. 2018-083006, filed Apr. 24, 2018, each of which is incorporated by reference herein in its entirety for all purposes.

TECHNICAL FIELD

The present invention relates to a preparation containing a polycyclic pyridone compound that is excellent in stability and suspensibility in water. Specifically, the present invention relates to a solid dosage form containing a stabilizer, a sugar alcohol and/or a sugar, a water soluble polymer and an inorganic substance, more specifically, a preparation containing a polycyclic pyridone compound that contains sodium chloride as a stabilizer, maltitol and mannitol as a sugar alcohol and/or a sugar, hypromellose as a water-soluble polymer, and light anhydrous silicic acid and talc as an inorganic substance and is improved in the stability of the polycyclic pyridone compound, the suspensibility of the preparation in water and the fluidity of the preparation.

BACKGROUND ART

Influenza is an acute respiratory infectious disease caused by infection with influenza virus. In Japan, there are millions of reports of patients with influenza-like diseases every winter, and influenza exhibits high morbidity and high mortality.

As anti-influenza drugs, Symmetrel (tradename: Amantadine) and Flumadine (tradename: Rimantadine) inhibiting virus uncoating process, and neuraminidase inhibitors suppressing budding/release of the virus from a cell such as Oseltamivir (tradename: Tamiflu) and Zanamivir (tradename: Relenza) are known. There are, however, problems of appearance of resistant strains and adverse reactions, and there is a possibility of a worldwide epidemic of highly pathogenic and highly mortal new influenza strains, and therefore, there is a demand for development of an anti-influenza drug of a novel mechanism.

Since a cap-dependent endonuclease which is an influenza virus-derived enzyme is essential for virus proliferation, and has the virus-specific enzymatic activity which is not possessed by a host, it is believed that the endonuclease is suitable for a target of an anti-influenza drug.

As a compound inhibiting the cap-dependent endonuclease, a compound represented by formula (II):

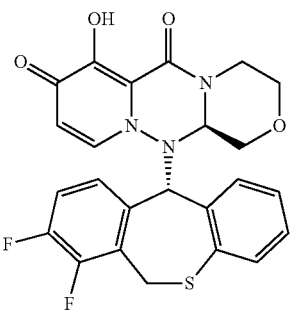

is described in Patent Literature 1, and this compound is useful as a compound having antiviral activity, particularly, having inhibitory activity for influenza virus proliferation.

When the compound represented by formula (II) is administered (for example, oral administration) to a living body, it is necessary to provide a compound that is more efficiently absorbed into the body to show a high pharmacological effect and to shorten disease duration of the influenza, and for these purposes, a compound represented by formula (I), that is, a prodrug of the compound represented by formula (II), is provided. The compound represented by formula (I):

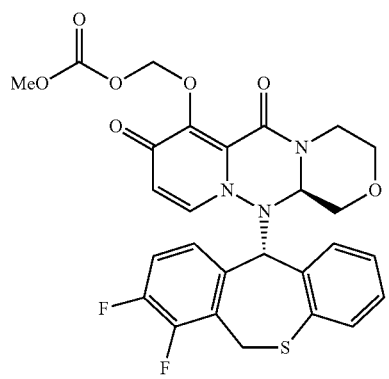

is also disclosed in Patent Literature 1.

Influenza is particularly a significant disease in high risk populations such as the infants and the elderly. Particularly, among currently commercially available anti-influenza drugs, a pediatric preparation for internal use is only Oseltamivir (tradename: Tamiflu), and there is a demand for development of a pediatric preparation for internal use of an anti-influenza drug.

A preparation for internal use includes a dry syrup, a fine granule, a tablet, a syrup, and the like. As a drug concentration in the preparation is lower, the amount of related substances may increase, depending on the drug, when a temporal stability test is conducted. Also, a pediatric preparation for internal use may be suspended in water in order for a child to take the preparation, and a drug may accumulate on the bottom of a container if suspensibility in water is poor. Furthermore, if the fluidity of a dry syrup or a fine granule is poor, the production thereof may be hindered. Accordingly, it is necessary to develop a pediatric preparation for internal use that has a small amount of related substances after a temporal stability test and further has good suspensibility in water and fluidity.

Patent Literatures 2 to 4, for example, disclose a granule with suppressed bitterness or improved drug absorbability containing sodium chloride. A compound used in each of Patent Literatures 2 to 4 is, for example, largely different from the compound represented by formula (I) in the chemical structure, and it is unclear whether formulation described in each of Patent Literatures 2 to 4 can improve the stability of the compound represented by formula (I), which is neither disclosed nor suggested.

Moreover, Patent Literature 5, for example, discloses a powder containing a specific compound, hypromellose and mannitol. A compound used in Patent Literature 5 is, for example, largely different from the compound represented by formula (I) in the chemical structure, and it is unclear whether formulation described in Patent Literature 5 results in excellent suspensibility in water of a solid dosage form containing the compound represented by formula (I), which is neither disclosed nor suggested.

PATENT LITERATURE

[Patent Literature 1] International Publication No. WO2016/175224, wherein the English equivalent application of this Publication is U.S. Pat. No. 10,392,406, which is incorporated by reference herein in its entirety for all purposes.

[Patent Literature 2] Japanese Patent Laid-Open No. 2008-07420, which is incorporated by reference herein in its entirety for all purposes.

[Patent Literature 3] Japanese Patent Laid-Open No. 2016-79102, which is incorporated by reference herein in its entirety for all purposes.

[Patent Literature 4] National Publication of International Patent Application No. 2001-512433, wherein the English equivalent application of this Japanese patent is U.S. Patent Application Publication No. 2003/0017210, which is incorporated by reference herein in its entirety for all purposes.

[Patent Literature 5] National Publication of International Patent Application No. 2014-534215, wherein the English equivalent application of this Japanese patent is U.S. Patent Application Publication No. 2014/0255505, which is incorporated by reference herein in its entirety for all purposes.

BRIEF SUMMARY OF THE INVENTION

An object of the present invention is to find a solid dosage form that has excellent stability of a compound represented by formula (I) and further excellent suspensibility in water.

In order to solve the above-described problems, the present inventors have made earnest studies resulting in finding that the stability of a polycyclic pyridone compound, the suspensibility of a preparation in water and the fluidity of the preparation are improved by containing one or more substance selected from the group consisting of an alkali metal chloride, an organic acid, a polyhydric alcohol ester and a fatty acid ester as a stabilizer, a sugar alcohol and/or a sugar, a water-soluble polymer and an inorganic substance, and thus the present invention was accomplished. Hereinafter, a preparation thus accomplished by the present invention is sometimes referred to as the "present preparation".

Specifically, the present invention relates to the following:

(1) A solid dosage form comprising a compound represented by formula (I):

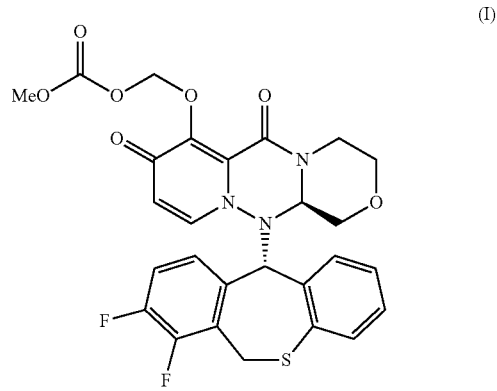 [SMILES: COC(=O)OCOc1c2n(ccc1=O)N([C@@H]1c3ccccc3SCc3c1ccc(F)c3F)[C@@H]1COCCN1C2=O]

or a pharmaceutically acceptable salt thereof, and one or more substance selected from the group consisting of an alkali metal chloride, an organic acid, a polyhydric alcohol ester and a fatty acid ester;

(2) the solid dosage form according to (1) above, which comprises an alkali metal chloride, and the alkali metal chloride is sodium chloride and/or potassium chloride;

(3) the solid dosage form according to (1) above, which comprises an organic acid, and the organic acid is ascorbic acid and/or fumaric acid;

(4) the solid dosage form according to (1) above, which comprises a polyhydric alcohol ester, and the polyhydric alcohol ester is one or more substance selected from the group consisting of Miglyol, triethyl citrate and polyoxyethylene sorbitan monooleate;

(5) the solid dosage form according to (1) above, which comprises a fatty acid ester, and the fatty acid ester is triacetin;

(6) the solid dosage form according to any one of (1) to (5) above, further comprising a sugar alcohol and/or a sugar;

(7) the solid dosage form according to (6) above, wherein the sugar alcohol and/or the sugar is one or more substance selected from the group consisting of isomalt, hydrogenated maltose starch syrup (maltitol), mannitol, xylitol, erythritol, sorbitol, lactose, sucrose, fructose, maltose, purified white sugar and trehalose;

(8) the solid dosage form according to any one of (1) to (7) above, comprising furthermore a water soluble polymer;

(9) the solid dosage form according to (8) above, wherein the water-soluble polymer is a cellulose-based polymer;

(10) a solid dosage form comprising a compound represented by formula (I):

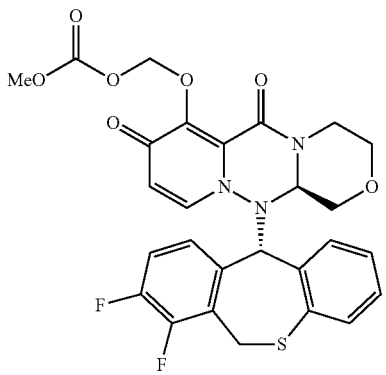

or a pharmaceutically acceptable salt thereof, and a cellulose-based polymer, provided that the solid dosage form contains no cellulose-based polymer in a coating layer;

(11) the solid dosage form according to (9) or (10) above, wherein the cellulose-based polymer is one or more substance selected from the group consisting of hypromellose, hydroxypropyl cellulose, methyl cellulose, carboxymethyl cellulose, carboxymethyl ethyl cellulose, hypromellose phthalate and hydroxypropyl methyl cellulose acetate succinate;

(12) the solid dosage form according to (11) above, wherein the cellulose-based polymer is hypromellose;

(13) the solid dosage form according to any one of (1) to (12) above, comprising furthermore an inorganic substance, provided that the solid dosage form contains no inorganic substance in a coating layer;

(14) the solid dosage form according to (13) above, wherein the inorganic substance is one or more substance selected from the group consisting of hydrated silicon dioxide, light anhydrous silicic acid and talc; and

(15) the solid dosage form according to any one of (1) to (14) above, wherein the release rate of the compound represented by formula (I) or the pharmaceutically acceptable salt thereof is 80% or more after 15 minutes of initiation of dissolution test in the method of Dissolution Test (paddle method) stipulated in the Japanese Pharmacopoeia 17th edition.

(16) The solid dosage form according to any one of (1) to (15) above, contains 1 mg to 80 mg of compound represented by formula (I):

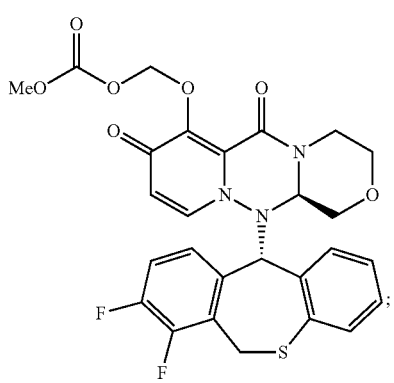

(17) The solid dosage form according to any one of (1) to (16) above, which is a granule or a dry syrup.

A preparation containing one or more stabilizer selected from the group consisting of an alkali metal chloride, an organic acid, a polyhydric alcohol ester and a fatty acid ester, a sugar alcohol and/or a sugar, a water-soluble polymer and an inorganic substance was able to reduce the amount of related substances of a polycyclic pyridone compound and to improve the fluidity of the preparation and the suspensibility of the preparation in water.

BRIEF DESCRIPTION OF THE DRAWINGS

FIG. 1 shows a powder X-ray diffraction pattern of the crystal of the compound represented by formula (I).

FIG. 2 shows dissolution profile of the compound represented by formula (I) at initiation of a temporal storage test and after a lapse of a prescribed period from initiation of the temporal storage test.

DETAILED DESCRIPTION OF THE INVENTION

As an active ingredient of the present preparation, a compound represented by formula (I):

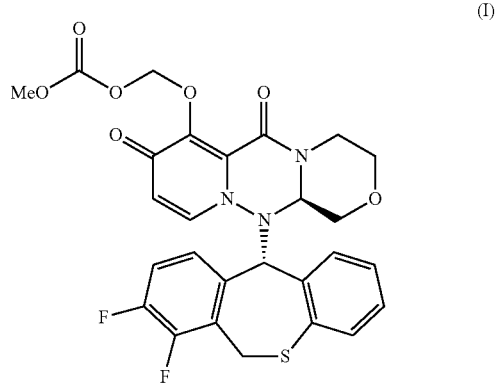 [SMILES: COC(=O)OCOc1c2n(ccc1=O)N([C@@H]1c3ccccc3SCc3c1ccc(F)c3F)[C@@H]1COCCN1C2=O]

or a pharmaceutically acceptable salt thereof is used.

A method for producing the compound represented by formula (I) or the pharmaceutically acceptable salt thereof is disclosed in Patent Literature 1.

The compound represented by formula (I) or the pharmaceutically acceptable salt thereof is converted into a compound represented by formula (II) in a living body, and has a cap-dependent endonuclease inhibitory activity. Accordingly, the compound represented by formula (I) or the pharmaceutically acceptable salt thereof is useful as an agent for treating and/or preventing influenza.

The compound represented by formula (I) or the pharmaceutically acceptable salt thereof is useful for symptoms and/or diseases induced by influenza virus. It is useful for treatment and/or prevention and symptom improvement of, for example, cold-like symptoms accompanied with fever, body chill, headache, muscle pain and general malaise, airway inflammation symptoms such as sore throat, nasal discharge, nasal congestion, cough and phlegm, gastrointestinal symptoms such as stomachache, vomiting and diarrhea, and complications accompanying secondary infection such as acute encephalopathy and pneumonia. In other words, the compound used in the present invention is useful for treatment and/or prevention of influenza virus infectious diseases.

The compound represented by formula (I) or the pharmaceutically acceptable salt thereof is useful for shortening disease duration of influenza. The disease duration of influenza can be shortened by, for example, about 20 to 40 hours or about 25 to 30 hours. Specifically, time necessary for improving "cough", "sore throat", "headache", "nasal congestion", "feverishness or body chill", "muscle or joint pain" and "fatigue" can be shortened. It is useful particularly for shortening the time necessary for improving "nasal congestion", "muscle or joint pain", "fatigue", "feverishness or body chill" and "headache". Besides, it is useful for shortening the time necessary for improving "nasal congestion" and "muscle or joint pain".

The compound represented by formula (I) or the pharmaceutically acceptable salt thereof has usefulness as a medical drug. The compound represented by formula (I) or the pharmaceutically acceptable salt thereof is a prodrug having advantages that it has high oral absorption, good bio availability and clearance and high distribution into lung, and hence can be an excellent medical drug.

The compound represented by formula (I) or the pharmaceutically acceptable salt thereof exhibits high metabolic stability and oral absorption and good bio-availability and clearance. Besides, the compound represented by formula (I) or the pharmaceutically acceptable salt thereof is highly distributed into lung and has a long half-life. Furthermore, the compound represented by formula (I) or the pharmaceutically acceptable salt thereof has advantages that it has a high non-protein binding rate and low hERG channel inhibition or CYP inhibition, exhibits a CPE (cytopathic effect) inhibitory activity, and/or is negative in phototoxicity test, Ames test and genotoxicity test, or it does not have toxicity causing liver damage or the like. Accordingly, a pharmaceutical composition of the compound used in the present invention can be an excellent medical drug.

A dose of the compound represented by formula (I) or the pharmaceutically acceptable salt thereof is varied depending on an administration method, the age, the weight and the state of a patient and the type of disease, and in employing oral administration, a dose of usually about 0.05 mg to 3000 mg, preferably about 0.1 mg to 1000 mg, and further preferably about 10 mg to 80 mg is administered to an adult per day dividedly if necessary. In employing parenteral administration, a dose of about 0.01 mg to 1000 mg, preferably about 0.05 mg to 500 mg, or more preferably about 1 mg to 80 mg is administered to an adult per day. Such a dose may be administered once or dividedly several times a day. Specifically, the content of the compound represented by formula (I) or the pharmaceutically acceptable salt thereof is 10 mg, 20 mg, 40 mg or 80 mg. In this case, 10 mg represents the range of 9.0 to 11.0 mg, preferably 9.5 to 10.5 mg, 20 mg represents the range of 18.0 to 22.0 mg, preferably 19.0 to 21.0 mg, 40 mg represents the range of 36.0 to 44.0 mg, preferably 38.0 to 42.0 mg, 80 mg represents the range of 72.0 to 88.0 mg, preferably 76.0 to 84.0 mg.

The compound represented by formula (I) or the pharmaceutically acceptable salt thereof can be used in combination with another drug or the like (hereinafter referred to as the concomitant drug) for purposes of enhancing the action of the compound or reducing the dose of the compound. For a disease of influenza, for example, it can be used in combination with a neuraminidase inhibitor (such as Oseltamivir, Zanamivir, Peramivir or Inavir), an RNA-dependent RNA polymerase inhibitor (such as Favipiravir), an M2 protein inhibitor (such as Amantadine), a PB2 cap-binding inhibitor (such as VX-787), an anti-HA antibody (such as MHAA4549A), or an immune agonist (such as nitazoxanide). In this case, administration periods of the compound and the concomitant drug employed in embodiments of the present invention are not limited, and these may be simultaneously administered to a subject of administration, or may be administered with a time lag. Besides, the compound represented by formula (I) or the pharmaceutically acceptable salt thereof and the concomitant drug may be administered in the form of two or more preparations respectively containing active ingredients, or may be administered in the form of a single preparation containing all the active ingredients.

The dose of the concomitant drug can be appropriately selected based on a clinically employed dose. Besides, a blending ratio between the compound represented by formula (I) or the pharmaceutically acceptable salt thereof and the concomitant drug can be appropriately selected depending on the subject of administration, the administration route, the target disease, the symptoms, a combination therebetween and the like. When the subject of administration is, for example, a human, the contaminant drug may be used in an amount of 0.01 to 100 parts by weight based on 1 part by weight of the compound represented by formula (I) or the pharmaceutically acceptable salt thereof.

The compound represented by formula (I) or the pharmaceutically acceptable salt thereof can be a pharmaceutical less likely to cause adverse reactions because it is a virus-specific enzyme having high inhibitory activity against cap structure-dependent endonuclease and hence has effects of high selectivity and the like.

Now, a method for specifying a compound represented by formula (I) or a crystal thereof, or a compound represented by formula (II) will be described.

Numerical values mentioned for ranges herein and in the appended claims are approximate values unless otherwise specified. Variation of numerical values is caused by factors such as device calibration, device error, an impurity of a substance, a crystal size and a sample size.

The term "crystal" as used here means a cyclic and anisotropic structure resulting from a structure in which atoms, ions, molecules or the like constituting a solid are regularly aligned. A crystal form and a degree of crystallinity can be measured any of various techniques including, for example, powder X-ray diffraction analysis, moisture adsorption/desorption analysis, differential scanning calorimetry, simultaneous thermogravimetric analysis, solution colorimetric analysis and solubility characteristics.

NMR analysis of a compound was performed at 300 MHz using DMSO-$d_6$ and $CDCl_3$.

Measurement of Powder X-ray Diffraction Pattern

In accordance with X-ray Powder Diffraction Method described in General Tests of The Japanese Pharmacopoeia, the crystal obtained in each example was subjected to powder X-ray diffraction analysis. Analysis conditions are as follows:

(Apparatus)
  MiniFlex 600 manufactured by Rigaku Corporation
(Operation Method)
  Detector: high-speed one-dimensional detector (D/Tec Ultra 2) and variable knife edge
  Measurement method: reflection method
  Type of light source: Cu
  Wavelength: CuKα radiation
  Tube current: 15 mA Tube voltage: 40 kV Sample plate: zero-background silicon holder Incident angle (θ) of X-rays: 4-40°, Sampling width: 0.02°

In general, an error occurs in a range of ±0.2° in a diffraction angle (2θ) in the powder X-ray diffraction, and therefore, the value of the diffraction angle embraces values falling in the range of about ±0.2°. Accordingly, not only a crystal completely the same in the diffraction angle at a peak in the powder X-ray diffraction but also a crystal the same in the diffraction angle at a peak with an error of about ±0.2° is also used in the present invention.

A content of the compound represented by formula (I) or the pharmaceutically acceptable salt thereof in the present preparation is 0.1 to 80% by weight, preferably 0.5 to 8% by weight, and more preferably 1 to 4% by weight based on the total amount of the preparation.

The present preparation may contain a stabilizer. Herein, as the stabilizer, those described in The Japanese Pharmacopoeia, The Japanese Pharmaceutical Codex, The Japanese Pharmaceutical Excipients, and The Japan's Specifications and Standards for Food Additives can be used, and particularly, those capable of stabilizing the compound represented by formula (I) or the pharmaceutically acceptable salt thereof during temporal storage can be used.

The stabilizer may be any substance that reduces the amount of related substances, particularly, the compound represented by formula (II), and specific examples include an alkali metal chloride, an organic acid, a polyhydric alcohol ester and a fatty acid ester.

The alkali metal chloride is an inorganic compound represented by chemical formula MX wherein M is an alkali metal, and X is chlorine. Specific examples include sodium chloride and potassium chloride, among which sodium chloride is preferred.

The organic acid is an organic compound having a carboxyl group (carboxylic acid), an organic compound having a sulfo group (sulfonic acid), or an organic compound having a hydroxy group, a thiol group, or enol as a characteristic group. Specific examples include formic acid, oxalic acid, acetic acid, citric acid, ascorbic acid and fumaric acid, among which ascorbic acid and fumaric acid are preferred, and fumaric acid is more preferred.

The polyhydric alcohol ester refers to an ester form of an alcohol having two or more hydroxy groups in the molecule, and the hydroxy groups are attached to separate carbon atoms in the polyhydric alcohol. Specific examples include Miglyol (medium-chain fatty acid triglyceride), triethyl citrate and polyoxyethylene sorbitan monooleate, among which Miglyol is preferred.

The fatty acid ester is a compound in which a carboxyl group of fatty acid is ester-bonded to an alcohol. Specific examples include triacetin (glyceryl triacetate), glycerin fatty acid ester, acyl glycerol, a monoglyceride derivative and polyglycerin fatty acid ester, among which triacetin is preferred.

The stabilizer of the present preparation may be blended in the preparation or may be coated on a surface of the preparation, and preferably, the stabilizer is blended in the preparation. When the stabilizer is blended in the preparation, it improves the stability of the compound represented by formula (I) contained in the preparation and can reduce the amount of related substances, particularly, the compound represented by formula (II).

A content of the stabilizer in the present preparation is 0.01 to 10% by weight, preferably 0.05 to 7.5% by weight, and more preferably 0.1 to 5% by weight based on the total amount of the preparation. When the content is smaller, there is a possibility that the amount of related substances increases.

The present preparation may contain an excipient. Herein, any excipients described in The Japanese Pharmacopoeia, The Japanese Pharmaceutical Codex, The Japanese Pharmaceutical Excipients, and The Japan's Specifications and Standards for Food Additives can be used as the excipient. Any excipient that offers good suspensibility of the preparation in water, also small adhesion of the preparation to a container, furthermore a high fine granule yield of the preparation and a small bulk density is preferred. Specific examples include a sugar alcohol and a sugar.

The sugar alcohol corresponds to a carbohydrate of the food labeling standards notified by Consumer Affairs Agency, Government of Japan, and is one kind of sugar generated by the reduction of a carbonyl group of aldose or ketose. Specific examples include isomalt, erythritol, D-mannitol, xylitol, sorbitol, hydrogenated maltose starch syrup (maltitol), lactitol, and oligosaccharide alcohol, among which D-mannitol and hydrogenated maltose starch syrup (maltitol) are preferred.

The sugar corresponds to a sugar of the food labeling standards notified by Consumer Affairs Agency, Government of Japan, and specific examples include monosaccharide and disaccharide, more specifically, xylose, glucose, fructose, maltose, lactose, sucrose, fructose, trehalose, isomerized sugar, syrup, purified white sugar, white sugar, purified sucrose spherical granule, anhydrous lactose, and sucrose/starch spherical granule, among which purified white sugar and white sugar are preferred.

As the excipient in the present preparation, a sugar alcohol and a sugar may be mixed and used. In this case, a sugar alcohol and a sugar may be combined, a sugar alcohol and another sugar alcohol may be combined, or a sugar and another sugar may be combined. The type and blending ratio of the sugar alcohol or the sugar to be combined may be any type and blending ratio that improves the suspensibility of the preparation in water and the adherence of the preparation to a container and offers a high fine granule yield of the preparation and a small bulk density. Specific examples of the combination include purified white sugar and hydrogenated maltose starch syrup (maltitol), purified white sugar and D-mannitol, and hydrogenated maltose starch syrup (maltitol) and D-mannitol, among which hydrogenated maltose starch syrup (maltitol) and D-mannitol are preferred. The blending ratio is 99:1 to 1:99, preferably 90:10 to 10:90, more preferably 80:20 to 20:80, and particularly preferably 75:25 to 25:75 in terms of weight ratio. More specifically, the ratio between hydrogenated maltose starch syrup (maltitol) and D-mannitol is 30:70 to 50:50.

The present preparation can contain an excipient other than a sugar alcohol or a sugar. Specific examples include polysaccharides such as oligosaccharide, dextrin and starch, semi digested starch, glucose hydrate, crystalline cellulose, microcrystalline cellulose, pullulan, δ-cyclodextrin, aminoethyl sulfonic acid, candy powder, sodium chloride, citric acid, sodium citrate, glycine, calcium gluconate, L-glutamine, tartaric acid, potassium hydrogen tartrate, ammonium carbonate, dextran 40, dextrin, calcium lactate, povidone, macrogol (polyethylene glycol) 1500, macrogol 1540, macrogol 4000, macrogol 6000, anhydrous citric acid, DL malic acid, sodium hydrogen phosphate, potassium dihydrogen phosphate, sodium dihydrogen phosphate, L-aspartic acid, alginic acid, carmellose sodium, hydrated silicon dioxide, crospovidone, calcium glycerophosphate, magnesium aluminosilicate, calcium silicate, magnesium silicate, light anhydrous silicic acid, synthetic aluminum silicate, flour, wheat starch, wheat germ flour, rice flour, rice starch, cellulose acetate phthalate, titanium oxide, magnesium oxide, dihydroxyaluminum aminoacetate, tribasic calcium phosphate, talc, calcium carbonate, magnesium carbonate, precipitated calcium carbonate, natural aluminum silicate, corn starch, granulated corn starch, potato starch, hydroxypropyl cellulose, hydroxypropyl starch, anhydrous calcium hydrogen phosphate, granulated anhydrous calcium hydrogen phosphate and calcium dihydrogen phosphate, which correspond to a carbohydrate of the food labeling standards notified by Consumer Affairs Agency, Government of Japan.

A content of the excipient in the present preparation is 1 to 99.5% by weight, preferably 5 to 99% by weight, and more preferably 10 to 98.5% by weight based on the total amount of the preparation. When the content is larger, there is the possibility that other components cannot be blended. When the content is smaller, there is a possibility that appearance of the preparation is influenced.

The present preparation is suspended in water, and the suspension can be taken. Particularly, in the case of administration to a child, such a medication method can be performed. It is, however, difficult to suspend the present preparation without a suspending agent. Thus, a suspending agent may be blended in the present preparation. Any suspending agents described in The Japanese Pharmacopoeia, The Japanese Pharmaceutical Codex, The Japanese Pharmaceutical Excipients, and The Japan's Specifications and Standards for Food Additives can be used as the suspending agent. Specific examples include cellulose-based polymers such as carmellose, carmellose sodium, crystalline cellulose/carmellose sodium, hydroxypropyl cellulose, hypromellose (hydroxypropyl methylcellulose), methyl cellulose, carboxymethyl ethyl cellulose, hydroxyethyl cellulose, hydroxyethyl methyl cellulose, hydroxypropyl methyl cellulose acetate succinate, hydroxypropyl methyl cellulose phthalate, and a fumaric acid/stearic acid/polyvinyl acetal diethylamino acetate/hydroxypropyl methyl cellulose mixture; acrylic-based polymers such as an ethyl acrylate/methyl methacrylate copolymer dispersion, an aminoalkyl methacrylate copolymer, a methacrylic acid copolymer, a 2-methyl-5-vinylpyridine methyl acrylate/methacrylic acid copolymer, a dried methacrylic acid copolymer, and a dimethyl aminoethyl methacrylate/methyl methacrylate copolymer; vinyl-based polymers such as polyvinyl pyrrolidone, crospovidone, a carboxyvinyl polymer, polyvinyl acetal diethylamino acetate, polyvinyl alcohol, a polyvinyl alcohol/methyl methacrylate/acrylic acid polymer, and a polyvinyl alcohol copolymer; sodium alginate, carrageenan, a carboxyvinyl polymer, a dried aluminum hydroxide gel, xanthan gum, magnesium aluminum silicate, sodium polyphosphate, macrogol 4000, and macrogol 6000, among which carmellose, carmellose sodium, crystalline cellulose/carmellose sodium, hydroxypropyl cellulose, hypromellose, and polyvinyl pyrrolidone are preferred, and hypromellose is more preferred. The suspending agent also plays a role as a dispersant that disperses the present preparation in water. However, in the case of forming a coating layer in the solid dosage form, the solid dosage form contains no cellulose-based polymer in the coating layer.

A content of the suspending agent in the present preparation is 0.01 to 10% by weight, preferably 0.05 to 7.5% by weight, and more preferably 0.1 to 5% by weight based on the total amount of the preparation. When the content is larger, there is a possibility that the preparation foams in water. When the content is smaller, there is a possibility that the preparation cannot be suspended in water.

A fluidizing agent may be blended in the present preparation in order to improve the fluidity of the preparation. Since there is a possibility that the amount of impurities or related substances increases depending on a fluidizing agent, it is necessary to select a fluidizing agent such that the amount of impurities or related substances does not increase. Any fluidizing agents described in The Japanese Pharmacopoeia, The Japanese Pharmaceutical Codex, The Japanese Pharmaceutical Excipients, and The Japan's Specifications and Standards for Food Additives can be used as the fluidizing agent, and typically, an inorganic substance a fatty acid, or a salt thereof is often selected. Specific examples include light anhydrous silicic acid, hydrated silicon dioxide, stearic acid, magnesium stearate, calcium stearate, and talc, among which light anhydrous silicic acid and hydrated silicon dioxide are preferred, and light anhydrous silicic acid is more preferred. However, in the case where the fluidizing agent is an inorganic substance and in the case of forming a coating layer in the solid dosage form, the solid dosage form contains no inorganic substance in the coating layer.

A content of the fluidizing agent in the present preparation is 0.01 to 10% by weight, preferably 0.05 to 7.5% by weight, and more preferably 0.1 to 5% by weight based on the total amount of the preparation. When the content is larger, there is a possibility that the amount of related substances increases. When the content is smaller, there is a possibility that the preparation does not fluidize and becomes an obstacle at the time of preparation.

A lubricant may be blended in the present preparation in order to improve the lubricity of the preparation. An index for selection of the lubricant is an angle of repose, and a smaller angle of repose means better fluidity. Any lubricants described in The Japanese Pharmacopoeia, The Japanese Pharmaceutical Codex, The Japanese Pharmaceutical Excipients, and The Japan's Specifications and Standards for Food Additives can be used as the lubricant, and typically, an inorganic substance, a fatty acid, or a salt thereof is often selected. Specific examples include light anhydrous silicic acid, hydrated silicon dioxide, sucrose fatty acid ester, stearyl alcohol, stearic acid, magnesium stearate, calcium stearate, sodium stearyl fumarate, and talc, among which light anhydrous silicic acid, hydrated silicon dioxide, and talc are preferred, and talc is more preferred. However, in the case where the lubricant is an inorganic substance and in the case of forming a coating layer in the solid dosage form, the solid dosage form contains no inorganic substance in the coating layer.

A content of the lubricant in the present preparation is 0.001 to 1% by weight, preferably 0.005 to 0.75% by weight, and more preferably 0.01 to 0.5% by weight based on the total amount of the preparation. When the content is larger, there is a possibility that the amount of related substances increases. When the content is smaller, the preparation does not fluidize and becomes an obstacle at the time of production.

A flavoring agent may be blended in the present preparation in order to correct the taste of an unpalatable (for example, bitter) drug as additives. Any flavoring agents described in The Japanese Pharmacopoeia, The Japanese Pharmaceutical Codex, The Japanese Pharmaceutical Excipients, and The Japan's Specifications and Standards for Food Additives can be used as the flavoring agent. Specific examples include ascorbic acid, aspartic acid, aspartame, sucralose, glycine, sodium chloride, magnesium chloride, hydrochloric acid, dilute hydrochloric acid, citric acid and a salt thereof, anhydrous citric acid, L-glutamic acid and a salt thereof, succinic acid and a salt thereof, acetic acid, tartaric acid and a salt thereof, sodium hydrogen carbonate, fumaric acid and a salt thereof, malic acid and a salt thereof, glacial acetic acid, disodium inosinate, honey, hydrogenated maltose starch syrup (maltitol), and powdered glycyrrhiza, among which sodium chloride is preferred.

A content of the flavoring agent in the present preparation is 0.01 to 10% by weight, preferably 0.05 to 7.5% by weight, and more preferably 0.1 to 5% by weight based on the total amount of the preparation. When the amount is larger or smaller, there is the possibility that unpleasant taste may occur when the preparation is taken.

The present preparation may contain a binder. Any binders described in The Japanese Pharmacopoeia, The Japanese Pharmaceutical Codex, The Japanese Pharmaceutical Excipients, and The Japan's Specifications and Standards for Food Additives can be used as the binder. Specific examples include hydroxypropyl cellulose, corn starch, pregelatinized starch, partially pregelatinized starch, gum arabic, gum arabic powder, gelatin, agar, dextrin, pullulan, polyvinyl pyrrolidone, polyvinyl alcohol, crystalline cellulose, methyl cellulose, ethyl cellulose, carboxymethyl ethyl cellulose, carmellose, carmellose sodium, hydroxyethyl cellulose, hydroxyethyl methyl cellulose, hydroxypropyl cellulose and hypromellose, among which polyvinyl pyrrolidone is preferred.

A content of the binder in the present preparation is 0.1 to 20% by weight, preferably 0.25 to 15% by weight, and more preferably 0.5 to 10% by weight based on the total amount of the preparation. When the content is larger, there is the possibility that the particle size of the preparation becomes too large. When the content is smaller, there is a possibility that the particle size of the preparation becomes too small.

The present preparation may contain a disintegrating agent. Any disintegrating agents described in The Japanese Pharmacopoeia, The Japanese Pharmaceutical Codex, The Japanese Pharmaceutical Excipients, and The Japan's Specifications and Standards for Food Additives can be used as the disintegrating agent. Specific examples include croscarmellose sodium, crospovidone, carmellose calcium, carboxymethyl starch sodium, and low substituted hydroxypropyl cellulose.

A content of the disintegrating agent in the present preparation is 0.5 to 20% by weight, preferably 0.75 to 15% by weight, and more preferably 1 to 10% by weight based on the total amount of the preparation.

The present preparation may contain a polymer. Any polymers described in The Japanese Pharmacopoeia, The Japanese Pharmaceutical Codex, The Japanese Pharmaceutical Excipients, and The Japan's Specifications and Standards for Food Additives can be used as the polymer. Specific examples include cellulose-based polymers such as hypromellose (hydroxypropyl methylcellulose), polyvinyl alcohol, ethyl cellulose, carboxymethyl ethyl cellulose, carmellose, carmellose sodium, hydroxyethyl cellulose, hydroxyethyl methyl cellulose, hydroxypropyl cellulose, hydroxypropyl methyl cellulose acetate succinate, hydroxypropyl methyl cellulose phthalate, and a fumaric acid/stearic acid/polyvinyl acetal diethylamino acetate/hydroxypropyl methyl cellulose mixture; acrylic-based polymers such as an ethyl acrylate/methyl methacrylate copolymer dispersion, an aminoalkyl methacrylate copolymer, a methacrylic acid copolymer, a 2-methyl-5-vinylpyridine methyl acrylate/methacrylic acid copolymer, a dried methacrylic acid copolymer, and a dimethyl aminoethyl methacrylate/methyl methacrylate copolymer; vinyl-based polymers such as polyvinyl pyrrolidone, crospovidone, a carboxyvinyl polymer, polyvinyl acetal diethylamino acetate, polyvinyl alcohol, a polyvinyl alcohol/methyl methacrylate/acrylic acid polymer, and a polyvinyl alcohol copolymer; and carnauba wax, stearyl alcohol, shellac and cetanol, among which hypromellose (hydroxypropyl methylcellulose) is preferred.

The present preparation may contain a colorant. Any colorants described in The Japanese Pharmacopoeia, The Japanese Pharmaceutical Codex, The Japanese Pharmaceutical Excipients, and The Japan's Specifications and Standards for Food Additives can be used as the colorant. Specific examples include iron oxide, a tar dye and a natural dye. Examples of the iron oxide include ferric oxide, yellow iron oxide, yellow ferric oxide and black iron oxide. Examples of the tar dye include Food Yellow No. 4 aluminum lake, Food Blue No. 1 aluminum lake, Food Red No. 3 aluminum lake, Food Blue No. 1, Food Blue No. 2, Food Yellow No. 4, Food Yellow No. 5, Food Red No. 102, Food Red No. 2 and Food Red No. 3. Examples of the natural dye include a turmeric extract, β-carotene, a carotene solution, sodium copper chlorophyllin, copper chlorophyll, a naked barley green leaf extract powder, a dried powder of green juice of naked barley green leaves, a naked barley green leaf extract, titanium oxide and talc. Examples of the dye include those used as the light stabilizer.

The present preparation may contain another additive if necessary in addition to those described above, and any additives described in The Japanese Pharmacopoeia, The Japanese Pharmaceutical Codex, The Japanese Pharmaceutical Excipients, and The Japan's Specifications and Standards for Food Additives can be used. Besides, a content of such an additive may be an arbitrary rate. Specific examples of the additive used in addition to those described above include a perfume and a sweetener.

Specific examples of the perfume include an orange extract, orange oil, caramel, camphor, cinnamon oil, spearmint oil, a strawberry extract, a chocolate extract, cherry flavor, spruce oil, pine oil, peppermint oil, vanilla flavor, strawberry flavor, a bitter extract, fruit flavor, a peppermint extract, mixture flavor, mint flavor, menthol, a lemon powder, lemon oil and rose oil, among which strawberry flavor is preferred.

Specific examples of the sweetener include aspartame, hydrogenated maltose starch syrup (maltitol), glycyrrhiza, xylitol, glycerin, saccharin, sucralose, D-sorbitol, acesulfame potassium, stevia, thaumatin, and advantame, among which sucralose is preferred.

The present preparation may be a solid dosage form. Specifically, it may be a granule, a dry syrup, a fine granule, a tablet, a powder, a capsule, a pill or the like, and is preferably a granule, a dry syrup or a fine granule and more preferably a granule.

A method for manufacturing a granule of the present preparation is not especially limited, and specifically is a method in which the active ingredients and additives such as a binder and an excipient are mixed to produce a mixed powder, and the mixed powder is granulated, and is preferably a wet granulation method in which granulation is performed with water, water containing a binder, a solvent or the like added, a dry granulation method in which compression molding is performed without using water, or a melt granulation method. As a machine to be used for mixing the active ingredients, additives and the like, a power mill, a V-shaped mixer, a container blender, or the like can be used. Besides, as a machine to be used for granulation, a wet pellet mill, a fluidized bed granulator, a stirring granulator, a dry crushing granulator, a melt extrusion granulator, or the like can be used.

When the present preparation is a granule, the average particle size of the granule is in the range of 1 to 1000 μm.

Preferable embodiments will now be described.

One embodiment provides a solid dosage form containing (1) a compound represented by formula (I) or a pharmaceutically acceptable salt thereof, and (2) one or more substance selected from the group consisting of an alkali metal chloride, an organic acid, a polyhydric alcohol ester and a fatty acid ester. Specific examples of the alkali metal chloride include sodium chloride and/or potassium chloride, and preferably sodium chloride. Specific examples of the organic acid include ascorbic acid and/or fumaric acid, and preferably fumaric acid. Specific examples of the polyhydric alcohol ester include Miglyol, triethyl citrate, and polyoxyethylene sorbitan monooleate. Specific examples of the fatty acid ester include triacetin.

Another embodiment provides a solid dosage form containing (1) a compound represented by formula (I) or a pharmaceutically acceptable salt thereof, (2) one or more substance selected from the group consisting of an alkali metal chloride, an organic acid, a polyhydric alcohol ester and a fatty acid ester, and (3) a sugar alcohol and/or a sugar. Specific examples of the alkali metal chloride include sodium chloride and/or potassium chloride, and preferably sodium chloride. Specific examples of the organic acid include ascorbic acid and/or fumaric acid, and preferably fumaric acid. Specific examples of the polyhydric alcohol ester include Miglyol, triethyl citrate, and polyoxyethylene sorbitan monooleate. Specific examples of the fatty acid ester include triacetin. Specific examples of the sugar alcohol and/or the sugar include one or more substance selected from the group consisting of isomalt, hydrogenated maltose starch syrup (maltitol), mannitol, xylitol, erythritol, sorbitol, lactose, sucrose, fructose, maltose, purified white sugar and trehalose, preferably one or more substance selected from the group consisting of purified white sugar, hydrogenated maltose starch syrup (maltitol) and D-mannitol, and more preferably hydrogenated maltose starch syrup (maltitol) and D-mannitol, and particularly, a mixture of hydrogenated maltose starch syrup (maltitol) and D-mannitol is preferred.

Still another embodiment provides a solid dosage form containing (1) a compound represented by formula (I) or a pharmaceutically acceptable salt thereof, (2) one or more substance selected from the group consisting of an alkali metal chloride, an organic acid, a polyhydric alcohol ester and a fatty acid ester, (3) a sugar alcohol and/or a sugar, and (4) a water-soluble polymer. Specific examples of the alkali metal chloride include sodium chloride and/or potassium chloride, and preferably sodium chloride. Specific examples of the organic acid include ascorbic acid and/or fumaric acid, and preferably fumaric acid. Specific examples of the polyhydric alcohol ester include Miglyol, triethyl citrate, and polyoxyethylene sorbitan monooleate. Specific examples of the fatty acid ester include triacetin. Specific examples of the sugar alcohol and/or the sugar include one or more substance selected from the group consisting of isomalt, hydrogenated maltose starch syrup (maltitol), mannitol, xylitol, erythritol, sorbitol, lactose, sucrose, fructose, maltose, purified white sugar and trehalose, preferably one or more substance selected from the group consisting of purified white sugar, hydrogenated maltose starch syrup (maltitol) and D-mannitol, and more preferably hydrogenated maltose starch syrup (maltitol) and D-mannitol, and particularly, a mixture of hydrogenated maltose starch syrup (maltitol) and D-mannitol is preferred. Specific examples of the water-soluble polymer include a cellulose-based polymer, an acrylic-based polymer, and a polyvinyl-based polymer, and preferably a cellulose-based polymer. More specific examples of the cellulose-based polymer include carmellose, carmellose sodium, crystalline cellulose/carmellose sodium, hydroxypropyl cellulose, hypromellose (hydroxypropyl methylcellulose), methyl cellulose, carboxymethyl ethyl cellulose, hydroxyethyl cellulose, hydroxyethyl methyl cellulose, hydroxypropyl methyl cellulose acetate succinate, hydroxypropyl methyl cellulose phthalate, and a fumaric acid/stearic acid/polyvinyl acetal diethylamino acetate/hydroxypropyl methyl cellulose mixture, and preferably hypromellose.

Still another embodiment provides a solid dosage form containing (1) a compound represented by formula (I) or a pharmaceutically acceptable salt thereof, (2) one or more substance selected from the group consisting of an alkali metal chloride, an organic acid, a polyhydric alcohol ester and a fatty acid ester, (3) a sugar alcohol and/or a sugar, (4) a water-soluble polymer, and (5) an inorganic substance. Specific examples of the alkali metal chloride include sodium chloride and/or potassium chloride, and preferably sodium chloride. Specific examples of the organic acid include ascorbic acid and/or fumaric acid, and preferably fumaric acid. Preferable examples of the polyhydric alcohol ester include Miglyol, triethyl citrate, and polyoxyethylene sorbitan monooleate. Specific examples of the fatty acid ester include triacetin. Specific examples of the sugar alcohol and/or the sugar include one or more substance selected from the group consisting of isomalt, hydrogenated maltose starch syrup (maltitol), mannitol, xylitol, erythritol, sorbitol, lactose, sucrose, fructose, maltose, purified white sugar and trehalose, preferably one or more substance selected from the group consisting of purified white sugar, hydrogenated maltose starch syrup (maltitol) and D-mannitol, and more preferably hydrogenated maltose starch syrup (maltitol) and D-mannitol, and particularly, a mixture of hydrogenated maltose starch syrup (maltitol) and D-mannitol is preferred. Specific examples of the water soluble polymer include a cellulose-based polymer, an acrylic-based polymer, and a polyvinyl-based polymer, and preferably a cellulose-based polymer. More specific examples of the cellulose-based polymer include carmellose, carmellose sodium, crystalline cellulose/carmellose sodium, hydroxypropyl cellulose, hypromellose (hydroxypropyl methylcellulose), methyl cellulose, carboxymethyl ethyl cellulose, hydroxyethyl cellulose, hydroxyethyl methyl cellulose, hydroxypropyl methyl cellulose acetate succinate, hydroxypropyl methyl cellulose phthalate, and a fumaric acid/stearic acid/polyvinyl acetal diethylamino acetate/hydroxypropyl methyl cellulose mixture, and preferably hypromellose. Specific examples of the inorganic substance include light anhydrous silicic acid, hydrated silicon dioxide, sodium stearyl fumarate, and talc, and preferably light anhydrous silicic acid and talc.

Still another embodiment provides a solid dosage form containing (1) a compound represented by formula (I) or a pharmaceutically acceptable salt thereof, and (2) a cellulose-based polymer. However, in the case of forming a coating layer in the solid dosage form, no cellulose-based polymer is contained in the coating layer. Specific examples of the cellulose-based polymer include carmellose, carmellose sodium, crystalline cellulose/carmellose sodium, hydroxypropyl cellulose, hypromellose (hydroxypropyl methylcellulose), methyl cellulose, carboxymethyl ethyl cellulose, hydroxyethyl cellulose, hydroxyethyl methyl cellulose, hydroxypropyl methyl cellulose acetate succinate, hydroxypropyl methyl cellulose phthalate, and a fumaric acid/stearic acid/polyvinyl acetal diethylamino acetate/hydroxypropyl methyl cellulose mixture, and preferably hypromellose.

Still another embodiment provides a solid dosage form containing (1) a compound represented by formula (I) or a pharmaceutically acceptable salt thereof, (2) a cellulose-based polymer, and (3) an inorganic substance. However, in the case of forming a coating layer in the solid dosage form, neither the cellulose-based polymer nor the inorganic substance is contained in the coating layer. Specific examples of the cellulose-based polymer include carmellose, carmellose sodium, crystalline cellulose/carmellose sodium, hydroxypropyl cellulose, hypromellose (hydroxypropyl methylcellulose), methyl cellulose, carboxymethyl ethyl cellulose, hydroxyethyl cellulose, hydroxyethyl methyl cellulose, hydroxypropyl methyl cellulose acetate succinate, hydroxypropyl methyl cellulose phthalate, and a fumaric acid/stearic acid/polyvinyl acetal diethylamino acetate/hydroxypropyl methyl cellulose mixture, and preferably hypromellose. Specific examples of the inorganic substance include light anhydrous silicic acid, hydrated silicon dioxide, sodium stearyl fumarate, and talc, and preferably light anhydrous silicic acid and talc.

The present preparation maintains suspensibility in water even when supplemented with water before use and left for a long time. For example, the suspension can be prepared by mixing the present preparation with water. In another embodiment, the suspension can be prepared by adding 20 mL of water to 2 g of the present preparation and mixing. Also, in another embodiment, the suspension can be prepared by measuring 20 mL of water and pouring them into the bottle, onto the present preparation. Then, gently swirl contents to avoid excess foaming and to assure the correct mixture of the present preparation and the water.

The suspensibility in water means that a visually uniform suspension is formed when 9.5 mL of water is added to about 1 g of the present preparation. Herein, these physical properties are sometimes collectively referred to as "uniform dispersibility". The present preparation hardly adheres to a container surface when added into the container.

The present preparation can prevent the sticking between preparations after storage. As an index for sticking of the preparation, the preparation is charged into a container, and the fluidity of the preparation after inversion can be confirmed.

The present preparation can enhance operation efficiency of production by improving fluidity. As an index for fluidity of the preparation, an angle of repose can be used.

The release rate of the compound represented by formula (I) or the pharmaceutically acceptable salt thereof from the present preparation is 75% or more, preferably 80% or more, and more preferably 85% or more after 15 minutes of initiation of dissolution test in the method of Dissolution Test (paddle method) stipulated by the Japanese Pharmacopoeia 17th edition.

The present preparation may be directly taken orally, or the present preparation is suspended in water or warm water, and then, the suspension of the present preparation may be taken. The present preparation may be taken not only by an adult but also by a child, and particularly, for a child, the present preparation is suspended in water or warm water, and then, the suspension of the present preparation can be taken.

EXAMPLES

Now, the present invention will be described in detail with reference to examples, comparative examples and reference examples, and it is noted that the present invention is not limited to these examples. A compound II can be produced by a method disclosed in International Publication No. WO2016/175224.

Example A Manufacturing Method for Compound I

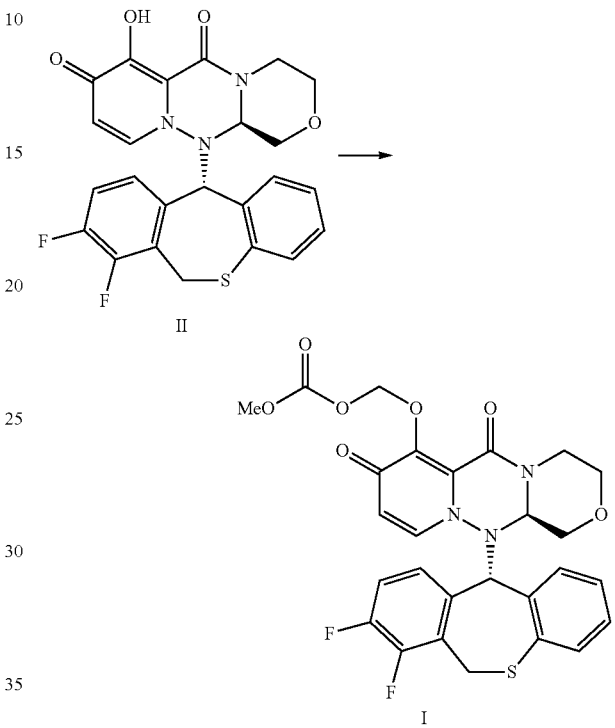

Potassium carbonate (1483.4 mg, 10.7 mmol), potassium iodide (549.5 mg, 3.3 mmol), tetrahydrofuran (33.1 g), N,N-dimethylacetamide (3.8 g) and water (80.3 mg) were added to the compound II (4.0 g, 8.3 mmol), followed by stirring. The resultant mixture was heated to 60° C., to which chloromethyl methyl carbonate (1758.9 mg, 14.2 mmol) was added. The resultant was stirred at 60° C. for 9 hours, and then cooled to 20° C. Acetic acid (822.0 mg), 2-propanol (3.1 g) and water (20.0 g) were added thereto, and the resultant was extracted twice with tetrahydrofuran (1.8 g, 8.9 g). The solvent was distilled off through vacuum concentration to a liquid weight of about 32 g. The resultant was heated to 45° C., 2-propanol (1.6 g) was added thereto, and the resultant was cooled to 20° C. A sodium acetate aqueous solution prepared from sodium acetate (339.0 mg) and water (46.0 g) was added thereto, followed by cooling to 5° C. After the resultant was stirred at 5° C. for 3 hours, a pale yellow precipitate was filtered off. The thus obtained solid was washed with a mixture of 2-propanol (4.7 g) and water (6.0 g), and the solid was then washed again with 2-propanol (6.3 g). To the thus obtained pale yellow solid, dimethyl sulfoxide (30.9 g) was added, followed by stirring. The resultant was heated to 60° C., to which a mixture of dimethyl sulfoxide (2.2 g) and water (4.8 g) was added. A mixture of dimethyl sulfoxide (19.9 g) and water (28.4 g) was further added thereto, followed by cooling to 20° C. After the resultant was stirred at 20° C. for 3 hours, a generated white precipitate was filtered off. The thus obtained solid was washed with a mixture of dimethyl sulfoxide (8.0 g) and water (4.8 g), and the solid was washed again with water (12.0 g). The thus obtained solid was dried to give a compound I (4.21 g) as white crystal.

$^1$H-NMR (DMSO-D6) δ: 2.91-2.98 (1H, m), 3.24-3.31 (1H, m), 3.44 (1H, t, J=10.4 Hz), 3.69 (1H, dd, J=11.5, 2.8 Hz), 3.73 (3H, s), 4.00 (1H, dd, J=10.8, 2.9 Hz), 4.06 (1H, d, J=14.3 Hz), 4.40 (1H, d, J=11.8 Hz), 4.45 (1H, dd, J=9.9, 2.9 Hz), 5.42 (1H, dd, J=14.4, 1.8 Hz), 5.67 (1H, d, J=6.5 Hz), 5.72-5.75 (3H, m), 6.83-6.87 (1H, m), 7.01 (1H, d, J=6.9 Hz), 7.09 (1H, dd, J=8.0, 1.1 Hz), 7.14-7.18 (1H, m), 7.23 (1H, d, J=7.8 Hz), 7.37-7.44 (2H, m)

Powder X-ray Diffraction: 2θ (°): Characteristic peaks are present at 8.6°±0.2°, 14.1°±0.2°, 17.4°±0.2°, 20.0°±0.2°, 24.0°±0.2°, 26.3°±0.2°, 29.6°±0.2° and 35.4°±0.2°.

The powder X-ray diffraction pattern of the crystal of compound I is shown in FIG. 1.

(1) Study on Stabilizer

In order to study a stabilizer, a stabilizer shown in each of Tables 2 to 4 and a compound represented by formula (I) were wet-granulated, and the amount of increase in the compound represented by formula (II), which is a related substance, were evaluated after a temporal stability test of the produced granule. A preparation having a formulation shown in Table 1 was produced by the stirring granulation method.

TABLE 1

|  | Content (mg) |
| --- | --- |
| Compound represented by Formula (I) | 2.0 |
| Purified White Sugar | 488.0 |
| Hydrogenated Maltose Starch Syrup (Maltitol) | 500.0 |
| Stabilizer | 30.0 |
| Hydroxypropyl Cellulose | 10.0 |
| Total | 1030.0 |

(Method for Manufacturing Preparation)

A compound represented by formula (I), purified white sugar, powdered hydrogenated maltose starch syrup (maltitol), a stabilizer and hydroxypropyl cellulose shown in Table 1 were mixed using a high-speed mixer (FS-GS SJT 10 high-speed mixer, Fukae Powtec Co., Ltd.), and water was added to the mixture, followed by stirring granulation. Then, the granulation product was subjected to size selection in a power mill (model P-3S, Showa Kagakukikai Co., Ltd.), and the resultant was dried at 65 to 70° C. in a fluidized bed granulator (WSG2&5 fluid bed dryer granulator, Okawara Mfg. Co., Ltd.). After drying, a granule was obtained by size selection in a power mill (model P-3S, Showa Kagakukikai Co., Ltd.). Granulation conditions in the high speed mixer were as follows:

(Granulation Conditions)
 Granulator: FS-GS SJT 10 high-speed mixer
 Rotational Speed of Agitator: 250 rpm
 Rotational Speed of Chopper: 2500 rpm
 Acceleration in Solution Injection: 21±2 g/min
 Moisture: 4 to 6.5% by weight
 Mashing time: 1 min±5 sec (Temporal Stability Test of Preparation)

The produced preparation was stored at 60° C. for 2 weeks, and the amount of increase in the compound represented by formula (II), which is a related substance, was measured.

(Stabilizer)

As shown in Tables 2 to 4, sodium chloride (Kanto Chemical Co., Inc.), potassium chloride (Wako Pure Chemical Industries, Ltd.), ascorbic acid (Nacalai Tesque, Inc.), fumaric acid (Merck KGaA), medium-chain fatty acid triglyceride Miglyol (Mitsuba Trading Co., Ltd.), triethyl citrate (Merck KGaA), sodium nitrite (Nacalai Tesque, Inc.), glycerin (Kanto Chemical Co., Inc.), and vitamin E (Merck KGaA) were used as the stabilizer.

TABLE 2

|  | Example 1 | Example 2 | Example 3 | Example 4 |
| --- | --- | --- | --- | --- |
| Stabilizer | Sodium Chloride | Potassium Chloride | Ascorbic Acid | Fumaric Acid |

TABLE 3

|  | Example 5 | Example 6 | Comparative Example 1 | Comparative Example 2 |
| --- | --- | --- | --- | --- |
| Stabilizer | Medium-Chain Fatty Acid Triglyceride Miglyol | Triethyl Citrate | Sodium Nitrite | Glycerin |

TABLE 4

|  | Comparative Example 3 | Comparative Example 4 |
| --- | --- | --- |
| Stabilizer | Vitamin E | None |

(Method for Measuring Compound Represented by Formula (II))

The amount of the compound represented by formula (II) was measured by liquid chromatography by employing the following method and conditions:
 Detector: ultraviolet absorptiometer (measurement wavelength: 260 nm)
 Column: XBridge C18, 3.5 μm, 3.0×150 mm
 Column temperature: constant temperature around 35° C.
 Mobile Phase A: 0.1% trifluoroacetic acid/0.2 mM EDTA solution, Mobile Phase B: acetonitrile
 Delivery of mobile phase: controlled for a concentration gradient with a mixing ratio between the mobile phase A and the mobile phase B changed as shown in Table 5

TABLE 5

| Time after Injection (min) | Mobile Phase A (vol %) | Mobile Phase B (vol %) |
| --- | --- | --- |
| 0-5 | 70 | 30 |
| 5-40 | 70→20 | 30→80 |
| 40-40.1 | 20→70 | 80→30 |

Flow rate: about 0.6 mL/min
Injection amount: 5 μL
Sample cooler temperature: about 5° C.
Washing solution for autoinjector: acetonitrile/methanol mixture (1:3)
Range of area measurement: 50 minutes after injection of sample solution
Equation for calculating amount of compound represented by formula (II):

Amount of compound represented by formula (II) (%)=(AII/ΣA$_T$)×100

ATII: peak area of compound represented by formula (II) in sample solution

ΣA$_T$: Sum of peak areas of sample solution (excluding blank and system peaks)

(Results)

The amount of increase (%) in the compound represented by formula (II) in the temporal stability test of the preparations of Examples 1 to 6 and Comparative Examples 1 to 4 is shown in Tables 6 to 8. As a result, the amount of increase (%) in the compound represented by formula (II) in the granules of Examples 1 to 6 was lower than that in the granule containing no stabilizer of Comparative Example 4. Particularly, the amount of increase in the compound represented by formula (II) in the granules containing sodium chloride of Example 1, ascorbic acid of Example 3, fumaric acid of Example 4 and medium chain fatty acid triglyceride Miglyol of Example 5 was much smaller than that in the granule containing no stabilizer of Comparative Example 4.

TABLE 6

|  | Example 1 | Example 2 | Example 3 | Example 4 |
|---|---|---|---|---|
| Stabilizer | Sodium Chloride | Potassium Chloride | Ascorbic Acid | Fumaric Acid |
| Amount of Increase (%) in Compound represented by Formula (II) | 0.70 | 1.31 | 0.28 | 0.30 |

TABLE 7

|  | Example 5 | Example 6 | Comparative Example 1 | Comparative Example 2 |
|---|---|---|---|---|
| Stabilizer | Medium-Chain Fatty Acid Triglyceride Miglyol | Triethyl Citrate | Sodium Nitrite | Glycerin |
| Amount of Increase (%) in Compound represented by Formula (II) | 0.34 | 1.24 | 6.63 | 9.95 |

TABLE 8

|  | Comparative Example 3 | Comparative Example 4 |
|---|---|---|
| Stabilizer | Vitamin E | None |
| Amount of Increase (%) in Compound represented by Formula (II) | 3.56 | 1.35 |

(2) Study on Excipient

In order to study an excipient, an excipient shown in each of Tables 9 to 11 and a compound represented by formula (I) were wet granulated, and the amount of increase in the compound represented by formula (II), which is a related substance, was evaluated after a temporal stability test of the produced granule.

(Method for Producing Preparation)

An excipient shown in each of Tables 9 to 11 and a compound represented by formula (I) were mixed in a bag at a ratio of 1:1, and then, the mixture was sieved through a 30-mesh sieve (wire diameter: 0.22 mm). The sieved mixed powder was mixed in a mortar, and then, purified water was gradually added such that moisture in granulation was about 5% by weight based on the charged amount of the materials, and the resultant was kneaded using a pestle. The kneaded product was subjected to wet size selection while pressed by hand through 16-mesh wires (wire diameter: 0.55 mm). The granulation product after the size selection was dried in a vented dryer, and a granule was prepared while pressed by hand through 20-mesh wires (wire diameter: 0.40 mm).

(Temporal Stability Test of Preparation)

The produced preparation was stored at 60° C. for 2 weeks, and the amount of increase in the compound represented by formula (II), which is a related substance, was measured.

(Excipient)

As shown in Tables 9 to 11, purified white sugar (Merck KGaA), hydrogenated maltose starch syrup (maltitol, ROQUETTE), D-mannitol (ROQUETTE), lactose hydrate (DMV-Fonterra Excipients GmbH & Co. KG), sorbitol (Merck KGaA), erythritol (ROQUETTE), xylitol (ROQUETTE), and isomalt (Beneo-Palatinit GmbH) were used as the excipient

TABLE 9

|  | Example 7 | Example 8 | Example 9 |
|---|---|---|---|
| Excipient | Purified White Sugar | Hydrogenated Maltose Starch Syrup (Maltitol) | D-Mannitol |

TABLE 10

|  | Reference Example 1 | Reference Example 2 | Reference Example 3 |
|---|---|---|---|
| Excipient | Lactose Hydrate | Sorbitol | Erythritol |

TABLE 11

|  | Reference Example 4 | Reference Example 5 |
|---|---|---|
| Excipient | Xylitol | Isomalt |

(Results)

The amount of increase (%) in the compound represented by formula (II) in the temporal stability test of the preparations of Examples 7 to 9 and Reference Examples 1 to 5, and the melting point of each excipient are shown in Tables 12 to 14. As a result, the amount of increase (%) in the compound represented by formula (II) in the granules of Examples 7 to 9 was slightly lower than that in the granules of Reference Examples 1, 2 and 5. The amount of increase (%) in the compound represented by formula (II) in the granules of Reference Examples 3 and 4 was almost the same as that in the granules of Examples 7 to 9, whereas the melting point was lower as compared with Examples 7 to 9 and thus, there was a possibility of sticking. Accordingly, it was regarded that purified white sugar, hydrogenated maltose starch syrup (maltitol) and D-mannitol are preferred as the excipient.

TABLE 12

|  | Example 7 | Example 8 | Example 9 |
|---|---|---|---|
| Excipient | Purified White Sugar | Hydrogenated Maltose Starch Syrup (Maltitol) | D-Mannitol |

TABLE 12-continued

|  | Example 7 | Example 8 | Example 9 |
|---|---|---|---|
| Melting point (° C.) | 160-186 | 145 | 166-168 |
| Amount of Increase (%) in Compound represented by Formula (II) | 0.08 | 0.06 | 0.11 |

TABLE 13

|  | Reference Example 1 | Reference Example 2 | Reference Example 3 |
|---|---|---|---|
| Excipient | Lactose Hydrate | Sorbitol | Erythritol |
| Melting point (° C.) | 160-186 | 145 | 166-168 |
| Amount of Increase (%) in Compound represented by Formula (II) | 0.17 | 0.15 | 0.08 |

TABLE 14

|  | Reference Example 4 | Reference Example 5 |
|---|---|---|
| Excipient | Xylitol | Isomalt |
| Melting point (° C.) | 92-96 | 141-161 |
| Amount of Increase (%) in Compound represented by Formula (II) | 0.04 | 0.38 |

(3) Study on Combination of Excipients

Although purified white sugar, hydrogenated maltose starch syrup (maltitol) and D-mannitol were selected as a preferable excipient, in order to study a combination of these excipients, a combination of excipients shown in each of Tables 15 and 16 and a compound represented by formula (I) were wet-granulated, and the produced granule was evaluated for (a) the amount of increase in the compound represented by formula (II), which is a related substance, (b) suspensibility in water, (c) container adherence, (d) a fine granule yield, and (e) a bulk density. A preparation having a formulation shown in each of Tables 15 and 16 was produced by the stirring granulation method.

TABLE 15

|  | Example 10 (weight mg) | Example 11 (weight mg) | Example 12 (weight mg) |
|---|---|---|---|
| Compound represented by Formula (I) | 10.0 | 20.0 | 10.0 |
| Maltitol | 300.0 | 350.0 | 490.0 |
| D-Mannitol | 614.0 | 554.0 | 490.0 |
| Purified White Sugar | — | — | — |
| Sodium Chloride | 30.0 | 30.0 | — |
| Polyvinyl Pyrrolidone k25 | 10.0 | 10.0 | 10.0 |
| Total | 964.0 | 964.0 | 1000.0 |
| Weight Ratio of Sugar or Sugar Alcohol | Maltitol:D-Mannitol = 32.8:67.2 | Maltitol:D-Mannitol = 38.7:61.3 | Maltitol:D-Mannitol = 50.0:50.0 |

TABLE 16

|  | Comparative Example 5 (weight mg) | Comparative Example 6 (weight mg) |
|---|---|---|
| Compound represented by Formula (I) | 10.0 | 10.0 |
| Maltitol | 500.0 | — |
| D-Mannitol | — | 500.0 |
| Purified White Sugar | 480.0 | 480.0 |
| Sodium Chloride | — | — |
| Polyvinyl Pyrrolidone k25 | 10.0 | 10.0 |
| Total | 1000.0 | 1000.0 |
| Weight Ratio of Sugar or Sugar Alcohol | Maltitol:Purified White Sugar = 51.0:49.0 | D-Mannitol:Purified White Sugar = 51.0:49.0 |

(Method for Producing Preparation)

A compound represented by formula (I), an excipient and polyvinyl pyrrolidone shown in each of Tables 15 and 16 were mixed using a high-speed mixer (LFS-GS-2J high-speed mixer, Fukae Powtec Co., Ltd.), and water was added to the mixture, followed by stirring granulation. Then, the granulation product was subjected to size selection in a power mill (model P-3S, Showa Kagakukikai Co., Ltd.), and the resultant was dried at 65 to 70° C. in a fluidized bed granulator (MP-01 Fluid bed dryer granulator, Powrex Corp.). After drying, a granule was obtained by size selection in a power mill (model P-3S, Showa Kagakukikai Co., Ltd.). Granulation conditions in the high-speed mixer were as follows:

(Granulation Conditions)
Granulator: LFS-GS-2J high-speed mixer
Rotational Speed of Agitator: 333 rpm
Rotational Speed of Chopper: 2500 rpm
Acceleration in Solution Injection: 20±3.5 g/min
Moisture: 3 to 7.5% by weight
Mashing time: 1 to 2 min±5 sec (Suspensibility Test of Preparation in Water)

The number of times of mix by inversion required for preparing a visually uniform suspension when 9.5 mL of water was added to about 1 g of the present preparation was recorded.

(Container Adherence of Preparation)

In the production of the present preparation, the amount of a granulation product adhering to the interior wall of a stirring granulator after granulation was visually confirmed. The presence or absence of adhesion after scraping off was evaluated as an index for container adherence.

(Fine Granule Yield Measurement of Preparation)

100 g of the present preparation was sieved through Nos. 30 and 140 sieves, and the ratio of the amount of a granule passing through the No. 30 sieve and remaining on the No. 40 sieve to the total amount of the sieved granule was calculated.

(Bulk Density Measurement of Preparation)

The present preparation was injected to a container (capacity: 100 mL) until overflowing, and the preparation was carefully leveled off to remove an excess from the upper surface of the container. The value of a preparation weight in the container was obtained from a container weight tared in advance, and a bulk density was determined according to the following equation:

Bulk density = Preparation weight in container/100

(Excipient)

As shown in Tables 15 and 16, purified white sugar (Merck KGaA), hydrogenated maltose starch syrup (maltitol, ROQUETTE), and D-mannitol (ROQUETTE) were used in combination as the excipient.

(Results)

The suspensibility in water, container adherence, fine granule yield and bulk density of the preparations of Examples 10 to 12 and Comparative Examples 5 and 6 are shown in Tables 17 and 18. As a result, the preparations of Examples 10 to 12 containing a mixture of hydrogenated maltose starch syrup (maltitol) and D-mannitol as an excipient had excellent suspensibility in water, small adherence to a container, and a bulk density of 0.5 g/mL or larger. Particularly, in Examples 10 and 11, the fine granule yield was also as high as 90% or more. On the other hand, the preparations of Comparative Examples 5 and 6 containing a mixture of purified white sugar and hydrogenated maltose starch syrup (maltitol) or purified white sugar and D-mannitol as an excipient were inferior in suspensibility in water to Examples and also had large container adherence. Particularly, in Comparative Example 6, the fine granule yield was also low.

TABLE 17

|  | Example 10 | Example 11 | Example 12 |
|---|---|---|---|
| Suspensibility in Water | Uniformly suspended by 15 times | Uniformly suspended by 10 times | Uniformly suspended by 10 times |
| Container Adherence | Small | Small | Small |
| Fine Granule Yield (%) | 92 | 90 | 72 |
| Bulk Density (g/mL) | 0.67 | 0.67 | 0.59 |

TABLE 18

|  | Comparative Example 5 | Comparative Example 6 |
|---|---|---|
| Suspensibility in Water | Uniformly suspended by 25 times | Uniformly suspended by 30 times |
| Container Adherence | Large | Large |
| Fine Granule Yield (%) | 89 | 66 |
| Bulk Density (g/mL) | 0.76 | 0.65 |

(4) Study on Binder

In order to study a binder, a binder shown in Table 19 and a compound represented by formula (I) were wet granulated, and the produced preparation was evaluated for (a) the amount of increase in the compound represented by formula (II), which is a related substance, after a temporal stability test and (b) a bulk density. A preparation having a formulation shown in Table 19 was produced by the stirring granulation method. Polyvinyl pyrrolidone K25 (BASF) and hydroxypropyl cellulose SL (Shin-Etsu Chemical Co., Ltd.) were used as the binder.

TABLE 19

|  | Example 13 (weight mg) | Example 14 (weight mg) | Reference Example 6 (weight mg) |
|---|---|---|---|
| Compound represented by Formula (I) | 10.0 | 10.0 | 10.0 |
| Purified White Sugar | 480.0 | 460.0 | 480.0 |
| Hydrogenated Maltose Starch syrup (Maltitol) | 500.0 | 500.0 | 500.0 |

TABLE 19-continued

|  | Example 13 (weight mg) | Example 14 (weight mg) | Reference Example 6 (weight mg) |
|---|---|---|---|
| Polyvinyl Pyrrolidone K25 | 10.0 | 30.0 | — |
| Hydroxypropyl Cellulose SL | — | — | 10.0 |
| Total | 1000.0 | 1000.0 | 1000.0 |

(Method for Producing Preparation)

A compound represented by formula (I), purified white sugar, hydrogenated maltose starch syrup (maltitol), and hydroxypropyl cellulose SL (Nippon Soda Co., Ltd.) or polyvinyl pyrrolidone K25 as a binder shown in Table 19 were mixed using a high speed mixer (LFS-GS-2J high speed mixer, Fukae Powtec Co., Ltd.), and water was added to the mixture, followed by stirring granulation. Then, the granulation product was subjected to size selection in a power mill (model P-3S, Showa Kagakukikai Co., Ltd.), and the resultant was dried at 65 to 70° C. in a fluidized bed granulator (MP-01 Fluid bed dryer granulator, Powrex Corp.). After drying, a granule was obtained by size selection in a power mill (model P-3S, Showa Kagakukikai Co., Ltd.). Granulation conditions in the high speed mixer were as follows:

(Granulation Conditions)
Granulator: LFS-GS-2J high-speed mixer
Rotational Speed of Agitator: 333 rpm
Rotational Speed of Chopper: 2500 rpm
Acceleration in Solution Injection: 20±3.5 g/min
Moisture: 3 to 7.5% by weight
Mashing time: 1 to 2 min±5 sec (Temporal Stability Test of Preparation)

The produced preparation was stored at 60° C. for 2 weeks, and the amount of increase in the compound represented by formula (II), which is a related substance, was measured.

(Bulk Density Measurement of Preparation)

The present preparation was injected to a container (capacity: 100 mL) until overflowing, and the preparation was carefully leveled off to remove an excess from the upper surface of the container. The value of a preparation weight in the container was obtained from a container weight tared in advance, and a bulk density was determined according to the following equation:

$$\text{Bulk density} = \text{Preparation weight in container}/100$$

(Results)

The amount of increase (%) in the compound represented by formula (II) in the temporal stability test of the preparations of Examples 13 and 14 and Reference Example 6, and the bulk density are shown in Table 20. As a result, the amount of increase (%) in the compound represented by formula (II) in the preparations of Examples 12 and 13 containing polyvinyl pyrrolidone was lower than that in the preparation of Reference Example 6 containing hydroxypropyl cellulose. The amount of increase (%) in the compound represented by formula (II) in the temporal stability test and the bulk density in the preparation of Example 12 in which the amount of polyvinyl pyrrolidone was 1% by weight were lower than those in the preparation of Example 13 in which the amount of polyvinyl pyrrolidone was 3% by weight.

TABLE 20

|  | Example 13 | Example 14 | Reference Example 6 |
|---|---|---|---|
| Amount of Increase (%) in Compound represented by Formula (II) | 0.12 | 0.15 | 0.20 |
| Bulk Density (g/mL) | 0.72 | 0.77 | — |

(5) Study on Fluidizing Agent

In order to study a fluidizing agent, (a) the amount of related substances after temporal storage of a preparation and (b) stickiness between preparations were evaluated. A preparation having a formulation shown in each of Tables 21 and 22 was produced by the stirring granulation method. 1% and 3% light anhydrous silicic acid (Cab-o-sil, CABOT Corp.), 1% and 3% hydrated silicon dioxide (RxCIPIENTS) and 1% and 3% sodium stearyl fumarate (PRUV, JRS Pharma) were used as the fluidizing agent.

TABLE 21

|  | Example 15 (weight mg) | Example 16 (weight mg) | Example 17 (weight mg) |
|---|---|---|---|
| Compound represented by Formula (I) | 10.0 | 10.0 | 10.0 |
| Hydrogenated Maltose Starch Syrup (Maltitol) | 490.0 | 490.0 | 490.0 |
| D-Mannitol | 490.0 | 490.0 | 490.0 |
| Polyvinyl Pyrrolidone k25 | 10.0 | 10.0 | 10.0 |
| Sucralose | 5.0 | 5.0 | 5.0 |
| Light Anhydrous Silicic Acid | 10.0 | 30.0 | — |
| Hydrated Silicon Dioxide | — | — | 10.0 |
| Sodium Stearyl Fumarate | — | — | — |
| Strawberry Flavor | 1.0 | 1.0 | 1.0 |
| Total | 1016.0 | 1036.0 | 1016.0 |

TABLE 22

|  | Example 18 (weight mg) | Comparative Example 7 (weight mg) | Comparative Example 8 (weight mg) |
|---|---|---|---|
| Compound represented by Formula (I) | 10.0 | 10.0 | 10.0 |
| Hydrogenated Maltose Starch Syrup (Maltitol) | 490.0 | 490.0 | 490.0 |
| D-Mannitol | 490.0 | 490.0 | 490.0 |
| Polyvinyl Pyrrolidone k25 | 10.0 | 10.0 | 10.0 |
| Sucralose | 5.0 | 5.0 | 5.0 |
| Light Anhydrous Silicic Acid | — | — | 10.0 |
| Hydrated Silicon Dioxide | 30.0 | — | — |
| Sodium Stearyl Fumarate | — | 10.0 | 30.0 |
| Strawberry Flavor | 1.0 | 1.0 | 1.0 |
| Total | 1036.0 | 1016.0 | 1036.0 |

(Method for Producing Preparation)

A compound represented by formula (I), hydrogenated maltose starch syrup (maltitol), D-mannitol, polyvinyl pyrrolidone K25, sucralose, a fluidizing agent (any of light anhydrous silicic acid, hydrated silicon dioxide, and sodium stearyl fumarate) and strawberry flavor shown in each of Tables 21 and 22 were mixed using a high-speed mixer (LFS-GS-2J high-speed mixer, Fukae Powtec Co., Ltd.), and water was added to the mixture, followed by stirring granulation. Then, the granulation product was subjected to size selection in a power mill (model P-3S, Showa Kagakukikai Co., Ltd.), and the resultant was dried at 65 to 70° C. in a fluidized bed granulator (MP-01 Fluid bed dryer granulator, Powrex Corp.). After drying, a granule was obtained by size selection in a power mill (model P-3S, Showa Kagakukikai Co., Ltd.). Granulation conditions in the high-speed mixer were as follows:

(Granulation Conditions)
Granulator: LFS-GS-2J high-speed mixer
Rotational Speed of Agitator: 333 rpm
Rotational Speed of Chopper: 2500 rpm
Acceleration in Solution Injection: 20±3.5 g/min
Moisture: 3 to 7.5% by weight
Mashing time: 1 to 2 min±5 sec (Temporal Stability Test of Preparation)

The produced present preparation was stored at 60° C. for 2 weeks, and the amount of increase in the compound represented by formula (II), which is a related substance, was measured.

(Stickiness Test of Preparation)

1 g of the preparation was charged into a 4 mL brown bottle, and evaluation was made as follows: good (indicated by circle), the preparation present at the bottom fluidized when the bottle was inverted three times; fair (indicated by triangle), the preparation present in an upper part fluidized when the bottle was inverted three times; and poor (indicated by x-mark), the preparation did not fluidize when the bottle was inverted three times.

(Results)

The amount of increase (%) in the compound represented by formula (II) in the temporal stability test of the preparations of Examples 15 to 18 and Comparative Examples 7 and 8, and the stickiness between preparations are shown in Tables 23 and 24. As a result, the amount of increase (%) in the compound represented by formula (II) in the preparations of Examples 15 to 18 was almost the same as that in the preparations of Comparative Examples 7 and 8 containing sodium stearyl fumarate, and was almost the same even when the amount of the fluidizing agent was changed.

Meanwhile, as a result of studying the stickiness of the preparations of Examples 15 to 18 and Comparative Examples 7 and 8, the preparations of Examples 15 to 18 had smaller stickiness than that of the preparations of Comparative Examples 7 and 8.

TABLE 23

|  | Example 15 | Example 16 | Example 17 |
|---|---|---|---|
| Amount of Increase (%) in Compound represented by Formula (II) | 0.64 | 0.51 | 0.34 |
| Stickiness | Δ | ○ | ○ |

TABLE 24

|  | Example 18 | Comparative Example 7 | Comparative Example 8 |
|---|---|---|---|
| Amount of Increase (%) in Compound represented by Formula (II) | 0.58 | 0.51 | 0.45 |
| Stickiness | ○ | x | x |

(6) Study on Suspending Agent

In order to study a suspending agent, the suspensibility of a preparation in water was evaluated. The present preparation having a formulation shown in Table 25 was produced by the stirring granulation method. Hypromellose (TC-5, Shin-Etsu Chemical Co., Ltd.), hydroxypropyl cellulose (HPC-L, Nippon Soda Co., Ltd.), and methyl cellulose (SM-4, Shin-Etsu Chemical Co., Ltd.) were used as the suspending agent.

TABLE 25

|  | Example 19 (weight mg) | Reference Example 7 (weight mg) | Reference Example 8 (weight mg) | Comparative Example 9 (weight mg) |
|---|---|---|---|---|
| Compound represented by Formula (I) | 20.0 | 20.0 | 20.0 | 20.0 |
| D-Mannitol | 564.0 | 564.0 | 564.0 | 564.0 |
| Hydrogenated Maltose Starch Syrup (Maltitol) | 350.0 | 350.0 | 350.0 | 353.0 |
| Sodium Chloride | 30.0 | 30.0 | 30.0 | 30.0 |
| Polyvinyl Pyrrolidone | 10.0 | 10.0 | 10.0 | 10.0 |
| Hypromellose | 3.0 | — | — | — |
| Hydroxypropyl Cellulose | — | 3.0 | — | — |
| Methyl Cellulose | — | — | 3.0 | — |
| Sucralose | 5.0 | 5.0 | 5.0 | 5.0 |
| Light Anhydrous Silicic Acid | 20.0 | 20.0 | 20.0 | 20.0 |
| Strawberry Flavor | 1.0 | 1.0 | 1.0 | 1.0 |
| Total | 1003.0 | 1003.0 | 1003.0 | 1003.0 |

(Method for Producing Preparation)

A compound represented by formula (I), D-mannitol, hydrogenated maltose starch syrup (maltitol), sodium chloride and polyvinyl pyrrolidone K25 shown in Table 25 were mixed using a vertical granulator (model VG-50, Powrex Corp.), and water was added to the mixture, followed by stirring granulation. Then, the granulation product was subjected to size selection in a power mill (model P-3S, Showa Kagakukikai Co., Ltd.), and the resultant was dried at 65 to 70° C. in a fluidized bed granulator (GPGC-15&30 fluid bed dryer granulator, Powrex Corp.). After drying, size selection was performed in a power mill (model P-3S, Showa Kagakukikai Co., Ltd.). The granulation product after the size selection was mixed with sucralose, a suspending agent (any of hypromellose, hydroxypropyl cellulose, and methyl cellulose), light anhydrous silicic acid and strawberry flavor using a V-shaped mixer (130 L V type blender, manufactured by Tokuju Corp.) to obtain a granule.

(Granulation Conditions)
Granulator: vertical granulator VG-50
Rotational Speed of Agitator: 200 rpm
Rotational Speed of Chopper: 2500 rpm
Acceleration in Solution Injection: 105±3 g/min
Moisture: 4.5 to 7.5% by weight
Mashing time: 1 to 3 min±5 sec (Suspensibility Test of Preparation in Water)

1 g of the present preparation was added into a stoppered container containing 9.5 mL of water, and the stoppered container was reciprocally inverted 40 times, and immediately thereafter, a liquid was collected from upper and lower parts of the container. After the completion of container inversion, the container was left at room temperature for 10 minutes, and a liquid was collected from a central part of the container. The concentration of the compound represented by formula (I) in the collected liquids was measured.

(Method for Measuring Compound Represented by Formula (I))

The amount of the compound represented by formula (I) was measured by liquid chromatography by employing the following method and conditions:
Detector: ultraviolet absorptiometer (measurement wavelength: 260 nm)
Column: ACQUITY UPLC BEH C18 1.7 μm, 2.1×50 mm (Waters Corp.)
Column temperature: constant temperature around 35° C.

Mobile Phase A: 0.1% trifluoroacetic acid/0.2 mM EDTA solution, Mobile Phase B: acetonitrile
Delivery of mobile phase: controlled for a concentration gradient with a mixing ratio between the mobile phase A and the mobile phase B changed as shown in Table 26.

TABLE 26

| Time after Injection (min) | Mobile Phase A (vol %) | Mobile Phase B (vol %) |
|---|---|---|
| 0-2.3 | 62 | 38 |
| 2.3-3 | 62 → 20 | 38 → 80 |
| 3-4 | 20 | 80 |

Flow rate: about 0.6 mL/min
Injection amount: 4 μL
Sample cooler temperature: about 5° C.
Washing solution for autoinjector: acetonitrile
Range of area measurement: 8 minutes after injection of sample solution
Equation for calculating amount of compound represented by formula (I):

Amount of compound represented by formula (I) (%)=MS/C×$A_T$/$A_S$×100

MS: weighed amount (mg)
C: labeled amount in preparation (mg/mL)
$A_S$: peak area obtained from standard solution
$A_T$: peak area obtained from sample solution (Evaluation of Suspensibility in Water)

The suspensibility of the preparation was evaluated according to the following equation:

Ratio (%) of amount of compound represented by formula (I) in suspension at central position of container after 10 minutes from container inversion = (Concentration of compound represented by formula (I) in suspension at central position of container after -continued 10 minutes from container inversion/Concentration of compound represented by formula (I) in suspension at central position of container immediately after container inversion} × 100(%)

(Results)

The suspensibility in water of the preparations of Example 19, Reference Examples 7 and 8, and Comparative Example 9 is shown in Table 27. As a result, the ratio of the amount of the compound represented by formula (I) in the suspensions of Example 19 and Reference Examples 7 and 8 was higher than that in the suspension of Comparative Example 9 containing no suspending agent. Particularly, the preparation of Example 19 containing hypromellose had a high ratio of the amount of the compound represented by formula (I) in the suspension and had good suspensibility in water.

TABLE 27

|  | Example 19 | Reference Example 7 | Reference Example 8 | Comparative Example 9 |
|---|---|---|---|---|
| Ratio (%) of amount of compound represented by formula (I) in suspension at central position of container after 10 minutes from container inversion | 95.1 | 93.0 | 92.9 | 65.8 |

(7) Study on Lubricant

In order to study a lubricant, an angle of repose was evaluated as an index for fluidity of a preparation. A preparation having a formulation shown in Table 28 was produced by the stirring granulation method. Talc (Merck KGAA, LUB) was used as the lubricant.

TABLE 28

|  | Example 20 (weight mg) | Comparative Example 10 (weight mg) |
|---|---|---|
| Compound represented by Formula (I) | 20.0 | 20.0 |
| D-Mannitol | 560.0 | 561.0 |
| Powdered Hydrogenated Maltose Starch Syrup (Maltitol) | 350.0 | 350.0 |
| Sodium Chloride | 30.0 | 30.0 |
| Polyvinyl Pyrrolidone | 10.0 | 10.0 |
| Hypromellose | 3.0 | 3.0 |
| Sucralose | 5.0 | 5.0 |
| Light Anhydrous Silicic Acid | 20.0 | 20.0 |
| Talc | 1.0 | — |
| Strawberry Flavor | 1.0 | 1.0 |
| Total | 1000.0 | 1000.0 |

(Method for Producing Preparation)

A compound represented by formula (I), D-mannitol, hydrogenated maltose starch syrup (maltitol), sodium chloride, polyvinyl pyrrolidone K25, and hypromellose shown in Table 28 were mixed using a vertical granulator (model FM-VG50, Powrex Corp.), and water was added to the mixture, followed by stirring granulation. Then, the granulation product was subjected to size selection in a power mill (model P-3S, Showa Kagakukikai Co., Ltd.), and the resultant was dried at 65 to 70° C. in a fluidized bed granulator (GPGC-15&30 fluid bed dryer granulator, Powrex Corp.). After drying, size selection was performed in a power mill (model P-3S, Showa Kagakukikai Co., Ltd.). The granulation product after the size selection was mixed with talc, sucralose, light anhydrous silicic acid and strawberry flavor using a V-shaped mixer (130 L V type blender, Tokuju Corp.) to obtain a granule.

(Granulation Conditions)
Granulator: vertical granulator VG-50
Rotational Speed of Agitator: 200 rpm
Rotational Speed of Chopper: 2500 rpm
Acceleration in Solution Injection: 105±3 g/min
Moisture: 4.5 to 7.5% by weight
Mashing time: 1 to 3 min±5 sec (Measurement of Angle of Repose of Preparation)

The angle of repose of the produced preparation was measured using a powder tester (Hosokawa Micron Group) under the following conditions:
Operation time: 170 sec, Slow down: 10 sec, Amplitude: 1.5 mm (Results)

The angle of repose of the preparations of Example 20 and Comparative Example 10 is shown in Table 29. As a result, the preparation of Example 20 containing talc had a smaller angle of repose than that of the preparation of Comparative Example 10 containing no talc, demonstrating that the fluidity of the preparation can be enhanced by containing talc.

TABLE 29

|  | Example 20 | Comparative Example 10 |
|---|---|---|
| Angle of Repose (°) | 33.7 | 36.2 |

(8) Measurement of Release Rate

The preparation of Example 20 shown in Table 28 was packaged with SP (aluminum) and stored at 25° C. and 60% relative humidity for 3, 6, 9, and 12 months, and the release rate of the compound represented by formula (I) was measured.

(Dissolution Property Test of Preparation)

The produced preparation was packaged with SP (aluminum) and stored at 25° C. and 60% relative humidity, and the release rate of the compound represented by formula (I) was measured by the second method of Dissolution Test described in the Japanese Pharmacopoeia (paddle method). The fluid used in the method of Dissolution Test was the dissolution test second fluid (containing Cetyltrimethylammonium Bromide), and the rotational speed of the paddle was set to 50 rpm.

(Results)

As shown in FIG. 2, the release rate from the preparation of Example 20 after storage at 25° C. and 60% relative humidity for 3, 6, 9, and 12 months hardly differed from the release rate from the preparation immediately after preparation.

(9) Preparation Having Different Content of Compound

Example 21 shown in Table 29 was prepared in the same manner of Example 20 by the stirring granulation method.

TABLE 30

|  | Example 21 (weight mg) |
|---|---|
| Compound represented by Formula (I) | 40.0 |
| D-Mannitol | 540.0 |

TABLE 30-continued

|  | Example 21 (weight mg) |
|---|---|
| Powdered Hydrogenated Maltose Starch Syrup (Maltitol) | 350.0 |
| Sodium Chloride | 30.0 |
| Polyvinyl Pyrrolidone | 10.0 |
| Hypromellose | 3.0 |
| Sucralose | 5.0 |
| Light Anhydrous Silicic Acid | 20.0 |
| Talc | 1.0 |
| Strawberry Flavor | 1.0 |
| Total | 1000.0 |

The present preparation containing the compound represented by formula (I) has been improved in stability, suspensibility in water, fluidity, etc. by various studies. This can suspend the present preparation in water, and the present preparation can be easily taken even by a child.

While the present preparation has been illustrated by a description of various embodiments, drawings and Examples, and while these embodiments, drawings and Examples have been described in detail, the present preparation is not limited to these embodiments, drawings and/or Examples in any way. Additional advantages and modifications will be readily apparent to those having ordinary skill in the art. Thus, the present preparation is not limited to the specific details, embodiments, drawings and Examples described herein.

The invention claimed is:

1. A solid dosage form comprising a compound represented by formula (I):

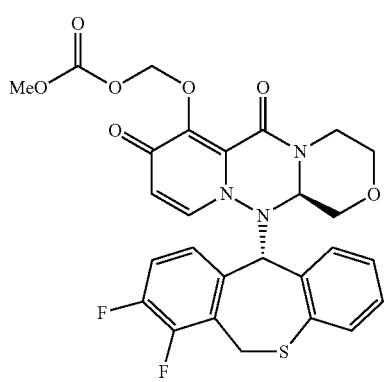

or a pharmaceutically acceptable salt thereof, maltitol, mannitol and one or more substances selected from the group consisting of an organic acid, a polyhydric alcohol ester, a fatty acid ester and a water-soluble polymer,
wherein the solid dosage form is in the form of a granule.

2. The solid dosage form according to claim 1, which comprises an organic acid, and the organic acid is at least one selected from the group consisting of ascorbic acid and fumaric acid.

3. The solid dosage form according to claim 1, which comprises a polyhydric alcohol ester, and the polyhydric alcohol ester is one or more substances selected from the group consisting of Miglyol, triethyl citrate, and polyoxyethylene sorbitan monooleate.

4. The solid dosage form according to claim 1, which comprises a fatty acid ester, and the fatty acid ester is triacetin.

5. The solid dosage form according to claim 1, which comprises a water-soluble polymer, and the water-soluble polymer is a cellulose-based polymer.

6. The solid dosage form according to claim 5, wherein the cellulose-based polymer is one or more substances selected from the group consisting of hypromellose, hydroxypropyl cellulose, methyl cellulose, carboxymethyl cellulose, carboxymethyl ethyl cellulose, hypromellose phthalate, and hydroxypropyl methyl cellulose acetate succinate.

7. The solid dosage form according to claim 1, wherein the solid dosage form does not comprise a coating layer.

8. The solid dosage form according to claim 1, comprising 1 mg to 80 mg of the compound represented by formula (I):

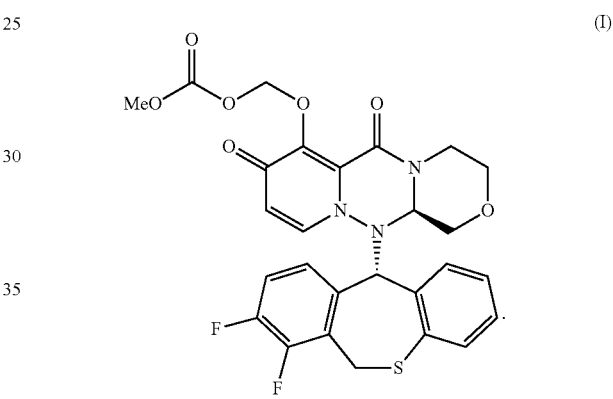

9. The solid dosage form according to claim 8, which comprises an organic acid, and the organic acid is ascorbic acid.

10. The solid dosage form according to claim 9, wherein the compound represented by formula (I) is present in an amount of 1 to 4% by weight based on the total weight of the solid dosage form.

11. The solid dosage form according to claim 10, comprising from 10 mg to 40 mg of the compound represented by formula (I).

12. The solid dosage form according to claim 8, which comprises an organic acid, and the organic acid is fumaric acid.

13. The solid dosage form according to claim 12, wherein the compound represented by formula (I) is present in an amount of 1 to 4% by weight based on the total weight of the solid dosage form.

14. The solid dosage form according to claim 13, comprising from 10 mg to 40 mg of the compound represented by formula (I).

* * * * *